(12) United States Patent
Bierman et al.

(10) Patent No.: US 9,138,252 B2
(45) Date of Patent: Sep. 22, 2015

(54) ACCESS DEVICE

(75) Inventors: Steven F. Bierman, Del Mar, CA (US); Richard A. Pluth, San Diego, CA (US)

(73) Assignee: Access Scientific, LLC, San Diego, CA (US)

( * ) Notice: Subject to any disclaimer, the term of this patent is extended or adjusted under 35 U.S.C. 154(b) by 0 days.

(21) Appl. No.: 13/526,369

(22) Filed: Jun. 18, 2012

(65) Prior Publication Data

US 2013/0123704 A1 May 16, 2013

Related U.S. Application Data

(63) Continuation of application No. 12/922,373, filed as application No. PCT/US2009/037198 on Mar. 13, 2009, now Pat. No. 8,202,251.

(60) Provisional application No. 61/036,900, filed on Mar. 14, 2008, provisional application No. 61/107,972, filed on Oct. 23, 2008.

(51) Int. Cl.
*A61M 25/00* (2006.01)
*A61B 17/34* (2006.01)
(Continued)

(52) U.S. Cl.
CPC ........ *A61B 17/3415* (2013.01); *A61M 25/0606* (2013.01); *A61M 25/0693* (2013.01); *A61M 25/09* (2013.01); *A61M 2025/09125* (2013.01)

(58) Field of Classification Search
CPC .................... A61M 25/0097; A61M 25/0606; A61M 25/0693; A61M 25/09; A61M 2025/09125; A61B 17/3415
USPC ........................................ 604/164.01, 164.13
See application file for complete search history.

(56) References Cited

U.S. PATENT DOCUMENTS

| 3,565,074 A | 2/1971 | Foti et al. |
| 3,995,628 A | 12/1976 | Gula et al. |
| 4,068,659 A | 1/1978 | Moorehead |

(Continued)

FOREIGN PATENT DOCUMENTS

| EP | 0139091 | 7/1984 |
| EP | 0502714 | 11/1995 |

(Continued)

OTHER PUBLICATIONS

A photograph of various access devices, Mar. 1, 2007.

(Continued)

*Primary Examiner* — Aarti B Berdichevsky
(74) *Attorney, Agent, or Firm* — Knobbe Martens Olson & Bear LLP

(57) ABSTRACT

An access device places a medical article within a body space of a patient. The device has a needle that includes an elongated body and a needle hub. The device further includes a dilator and a medical article. A track can extend in a proximal direction from the dilator. The needle hub can slide along at least a portion of the track between a first position and a second position. The device can further include a locking mechanism operably disposed between the track and the needle hub so as to inhibit further axial movement of the needle in the proximal direction when the needle hub is in the second position. The device can further include a guidewire that can bend such that the guidewire can both pass through the needle hub at one end and attach to the needle hub at another end.

19 Claims, 35 Drawing Sheets

(51) Int. Cl.
*A61M 25/06* (2006.01)
*A61M 25/09* (2006.01)

(56) References Cited

U.S. PATENT DOCUMENTS

| | | | |
|---|---|---|---|
| 4,205,675 A | 6/1980 | Vaillancourt |
| 4,230,123 A | 10/1980 | Hawkins, Jr. |
| 4,411,655 A | 10/1983 | Schreck |
| 4,417,886 A | 11/1983 | Frankhouser et al. |
| 4,512,351 A | 4/1985 | Pohndorf |
| 4,525,157 A | 6/1985 | Vaillancourt |
| 4,581,019 A | 4/1986 | Curelaru et al. |
| 4,629,450 A | 12/1986 | Susuki et al. |
| 4,655,750 A | 4/1987 | Vaillancourt |
| 4,661,300 A | 4/1987 | Daugherty |
| 4,772,264 A | 9/1988 | Cragg |
| 4,791,937 A | 12/1988 | Wang |
| 4,850,975 A | 7/1989 | Furukawa |
| 4,869,259 A | 9/1989 | Elkins |
| 4,894,052 A | 1/1990 | Crawford |
| 4,944,728 A | 7/1990 | Carrell |
| 4,955,890 A | 9/1990 | Yamamoto et al. |
| 4,961,729 A | 10/1990 | Vaillancourt |
| 4,978,334 A | 12/1990 | Toye et al. |
| 4,995,866 A | 2/1991 | Amplatz et al. |
| 5,066,284 A | 11/1991 | Mersch et al. |
| 5,108,374 A | 4/1992 | Lemieux |
| 5,114,401 A | 5/1992 | Stuart et al. |
| 5,171,218 A | 12/1992 | Fonger et al. |
| 5,242,410 A | 9/1993 | Melker |
| 5,246,426 A | 9/1993 | Lewis et al. |
| 5,250,038 A | 10/1993 | Melker et al. |
| 5,255,691 A | 10/1993 | Otten |
| 5,295,969 A | 3/1994 | Fischell |
| 5,295,970 A | 3/1994 | Clinton et al. |
| 5,306,253 A | 4/1994 | Brimhall |
| 5,312,355 A | 5/1994 | Lee |
| 5,328,480 A | 7/1994 | Melker et al. |
| 5,330,433 A | 7/1994 | Fonger et al. |
| 5,366,441 A | 11/1994 | Crawford |
| 5,380,290 A | 1/1995 | Makower et al. |
| 5,391,178 A | 2/1995 | Yapor |
| 5,512,052 A | 4/1996 | Jesch |
| 5,542,932 A | 8/1996 | Daugherty |
| 5,589,120 A | 12/1996 | Khan et al. |
| 5,676,689 A | 10/1997 | Kensey et al. |
| 5,688,249 A | 11/1997 | Chang et al. |
| 5,690,619 A | 11/1997 | Erskine |
| 5,704,914 A | 1/1998 | Stocking et al. |
| 5,728,132 A | 3/1998 | Van Tassel et al. |
| 5,795,339 A | 8/1998 | Erskine |
| 5,810,780 A | 9/1998 | Brimhall et al. |
| 5,820,596 A | 10/1998 | Rosen et al. |
| 5,827,202 A | 10/1998 | Miraki et al. |
| 5,830,190 A | 11/1998 | Howell |
| 5,833,662 A | 11/1998 | Stevens |
| 5,858,002 A | 1/1999 | Jesch |
| 5,885,217 A | 3/1999 | Gisselberg et al. |
| 5,885,253 A | 3/1999 | Liu |
| 5,904,657 A | 5/1999 | Unsworth et al. |
| 5,910,132 A | 6/1999 | Schultz |
| 5,919,160 A | 7/1999 | Sanfilippo |
| 5,935,110 A | 8/1999 | Brimhall |
| 6,027,480 A | 2/2000 | Davis et al. |
| 6,046,143 A | 4/2000 | Khan et al. |
| 6,074,377 A | 6/2000 | Sanfilippo |
| 6,080,141 A | 6/2000 | Castro et al. |
| 6,120,494 A | 9/2000 | Jonkman |
| 6,159,179 A | 12/2000 | Simonson |
| 6,179,813 B1 | 1/2001 | Ballow et al. |
| 6,210,366 B1 | 4/2001 | Sanfilippo |
| 6,273,871 B1 | 8/2001 | Davis et al. |
| 6,277,100 B1 | 8/2001 | Raulerson |
| 6,436,070 B1 | 8/2002 | Botich et al. |
| 6,461,362 B1 | 10/2002 | Halseth et al. |
| 6,475,207 B1 | 11/2002 | Maginot |
| 6,488,662 B2 | 12/2002 | Sirimanne |
| 6,500,152 B1 | 12/2002 | Illi |
| 6,524,277 B1 | 2/2003 | Chang |
| 6,607,511 B2 | 8/2003 | Halseth et al. |
| 6,641,564 B1 | 11/2003 | Kraus |
| 6,692,462 B2 | 2/2004 | Mackenzie et al. |
| 6,692,482 B2 | 2/2004 | Heller et al. |
| 6,726,659 B1 | 4/2004 | Stocking et al. |
| 6,808,520 B1 | 10/2004 | Fourkas et al. |
| 6,836,687 B2 | 12/2004 | Kelley |
| 6,905,481 B2 | 6/2005 | Sirimanne |
| 6,972,002 B2 | 12/2005 | Thorne |
| 6,994,693 B2 | 2/2006 | Tal |
| 7,001,396 B2 | 2/2006 | Glazier et al. |
| 7,025,746 B2 | 4/2006 | Tal |
| 7,192,433 B2 | 3/2007 | Osypka et al. |
| 7,270,649 B2 | 9/2007 | Fitzgerald |
| 7,556,617 B2 | 7/2009 | Voorhees, Jr. et al. |
| 7,722,567 B2 | 5/2010 | Tal |
| 7,887,516 B2 | 2/2011 | Young |
| 7,922,696 B2 | 4/2011 | Tal et al. |
| 8,105,286 B2 | 1/2012 | Anderson et al. |
| 8,192,402 B2 | 6/2012 | Anderson et al. |
| 2002/0072712 A1 | 6/2002 | Nool et al. |
| 2002/0087076 A1 | 7/2002 | Meguro et al. |
| 2003/0171718 A1 | 9/2003 | Delegge |
| 2004/0092879 A1 | 5/2004 | Kraus et al. |
| 2004/0171988 A1 | 9/2004 | Moretti |
| 2006/0129100 A1 | 6/2006 | Tal |
| 2007/0255211 A1 | 11/2007 | Young |
| 2009/0221961 A1 | 9/2009 | Tal et al. |
| 2011/0021994 A1 | 1/2011 | Anderson et al. |
| 2011/0202006 A1 | 8/2011 | Bierman et al. |
| 2011/0218496 A1 | 9/2011 | Bierman |
| 2011/0276002 A1 | 11/2011 | Bierman |
| 2012/0065590 A1 | 3/2012 | Bierman et al. |
| 2012/0316500 A1 | 12/2012 | Bierman et al. |

FOREIGN PATENT DOCUMENTS

| | | |
|---|---|---|
| KR | 10-2005-0027359 | 3/2005 |
| WO | WO 03/057272 | 7/2003 |
| WO | WO 2012/135761 | 10/2012 |
| WO | WO 2012/162677 | 11/2012 |
| WO | WO 2013/026045 | 2/2013 |

OTHER PUBLICATIONS

Arrow Trauma Products No. TRM-C 12/00 11M, Arrow International, dated 2000.
Photos of a peripheral emergency infusion device Applicant believes to be produced by Arrow International Inc., Jul. 20, 2011.
Photos of a splittable catheter design., Jul. 20, 2011.
Photos of an infusion device Applicant believes to be produced by B. Braun Medical Inc., Mar. 1, 2007.
Search Report and Written Opinion PCT/US2009/037198, Jun. 15, 2009.

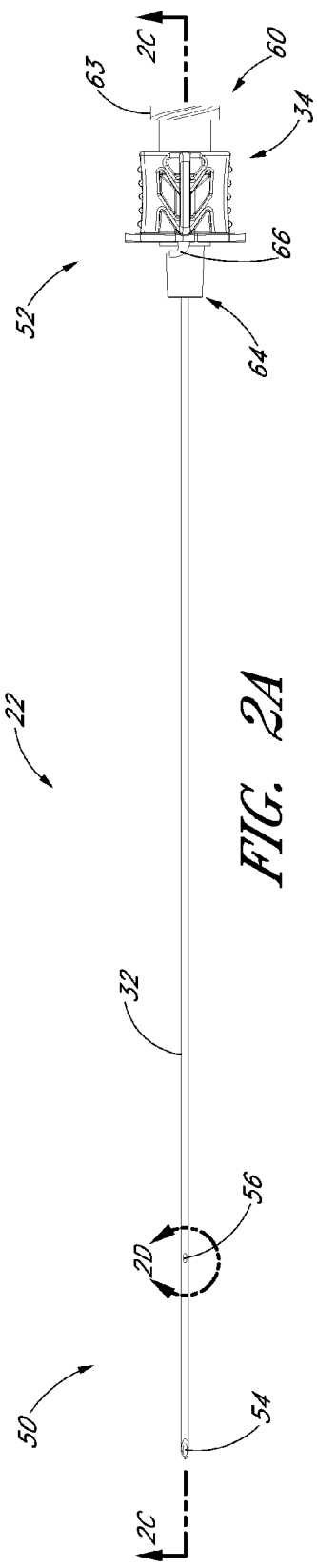
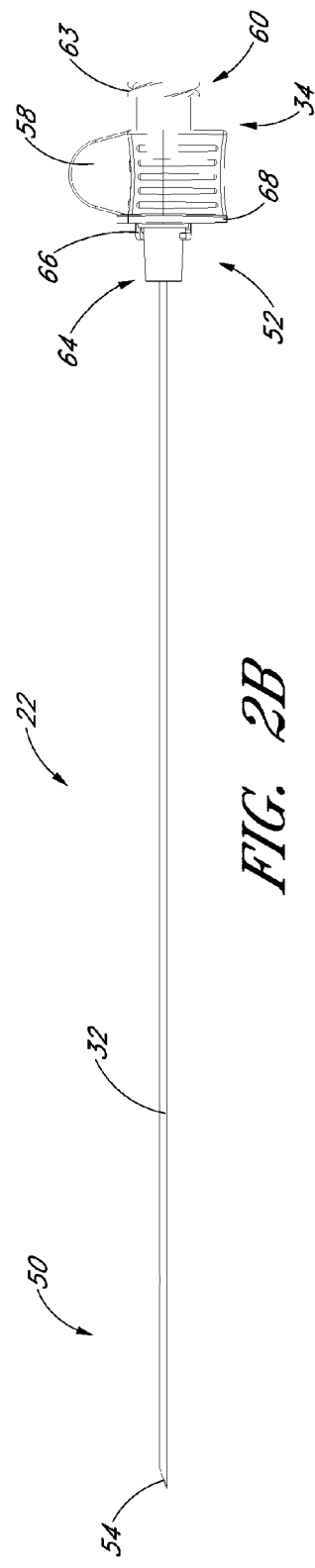
FIG. 2A
FIG. 2B

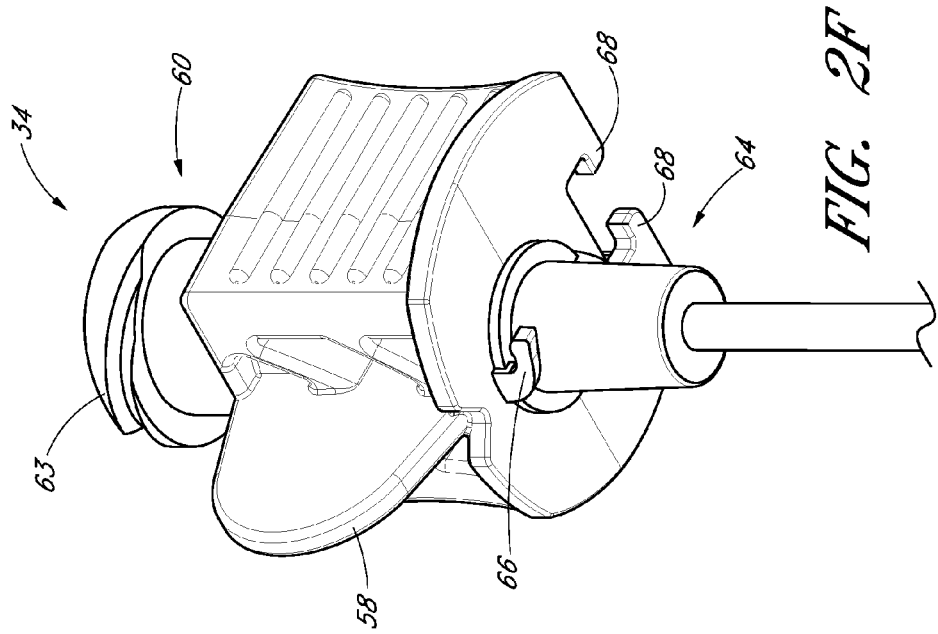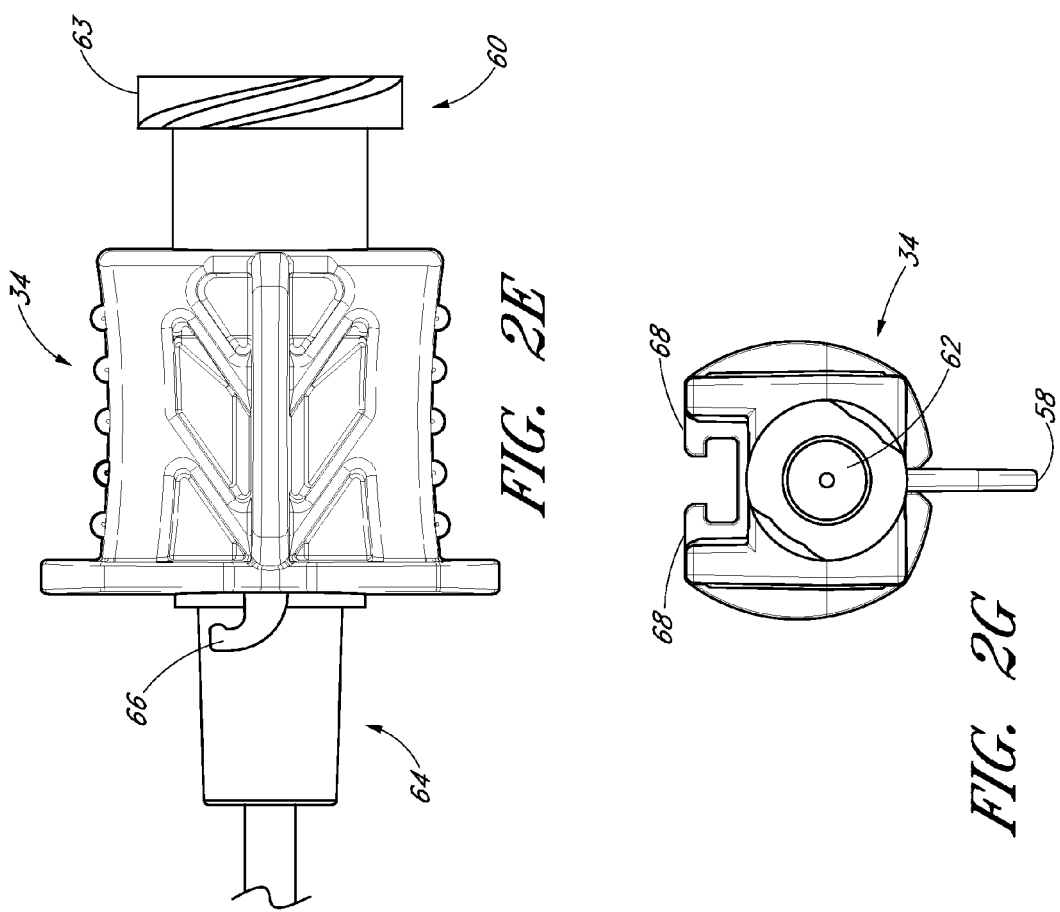

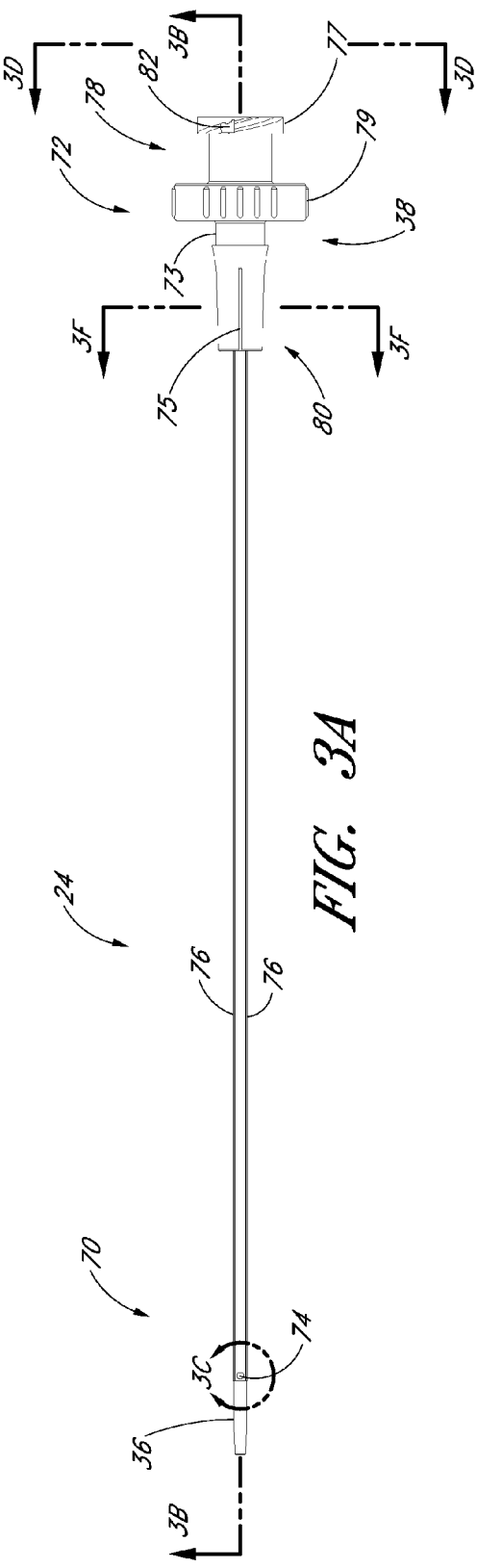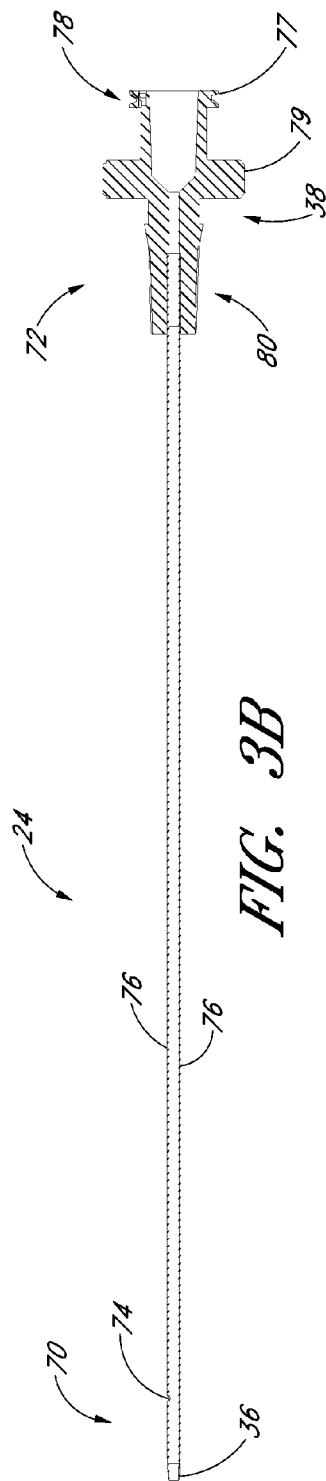
FIG. 3A
FIG. 3B

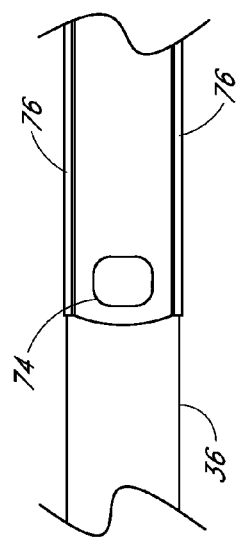
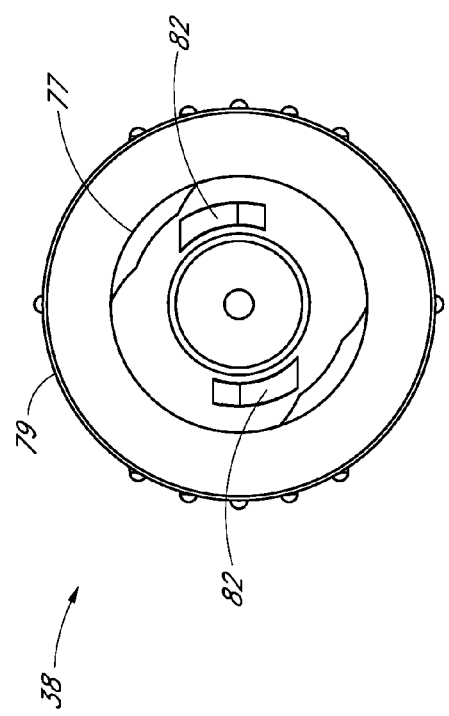

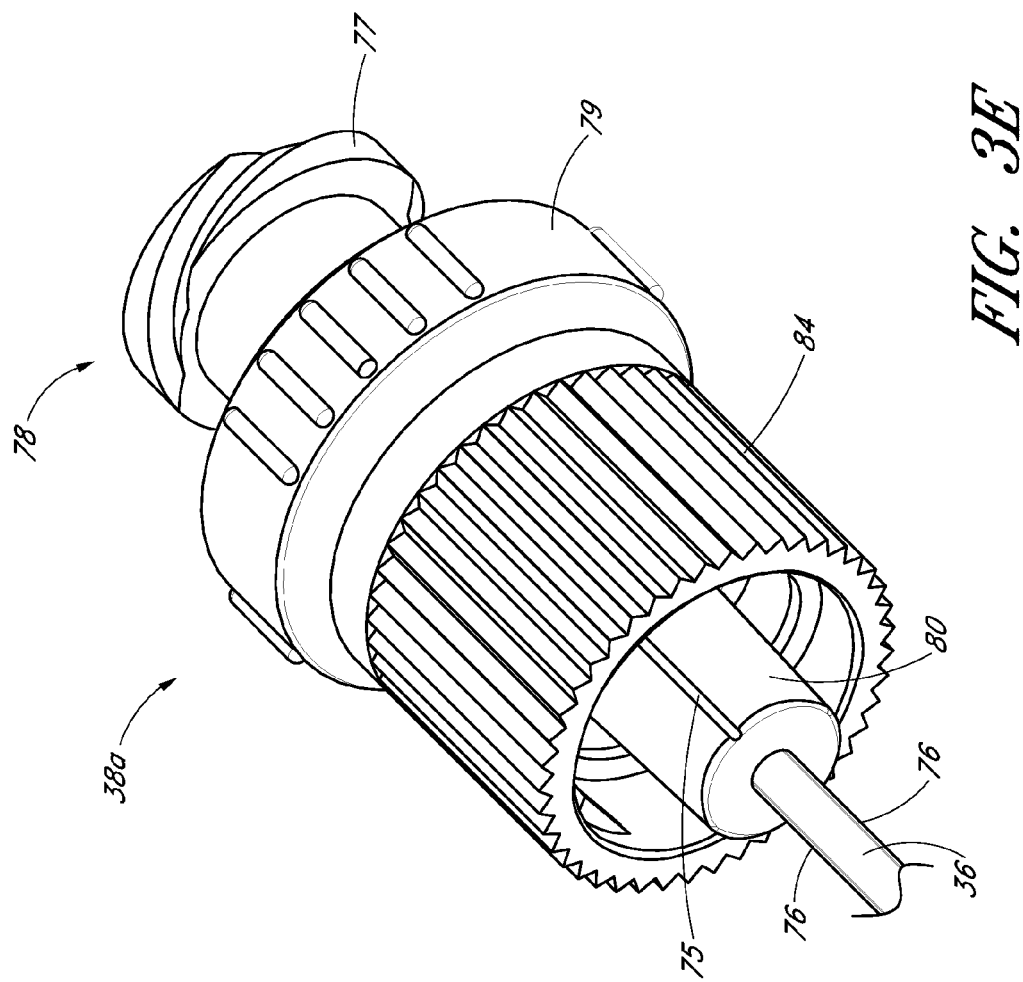

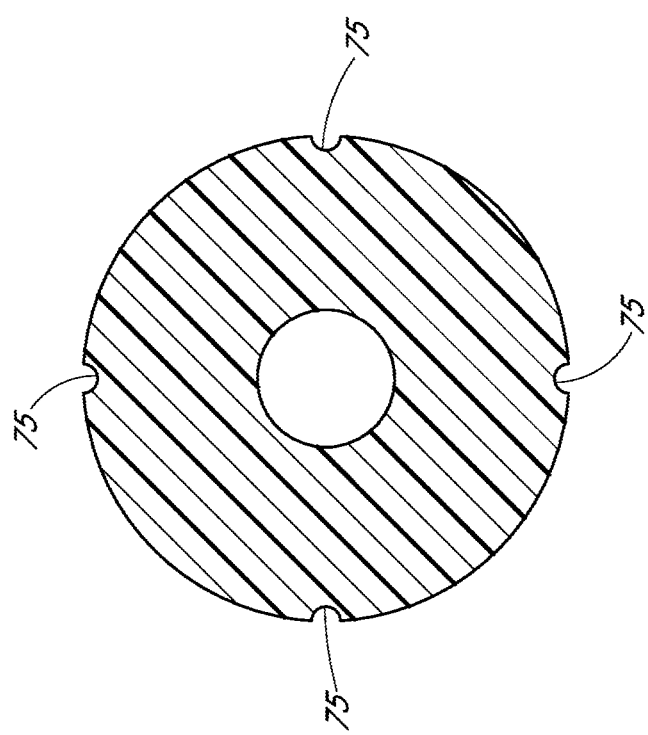

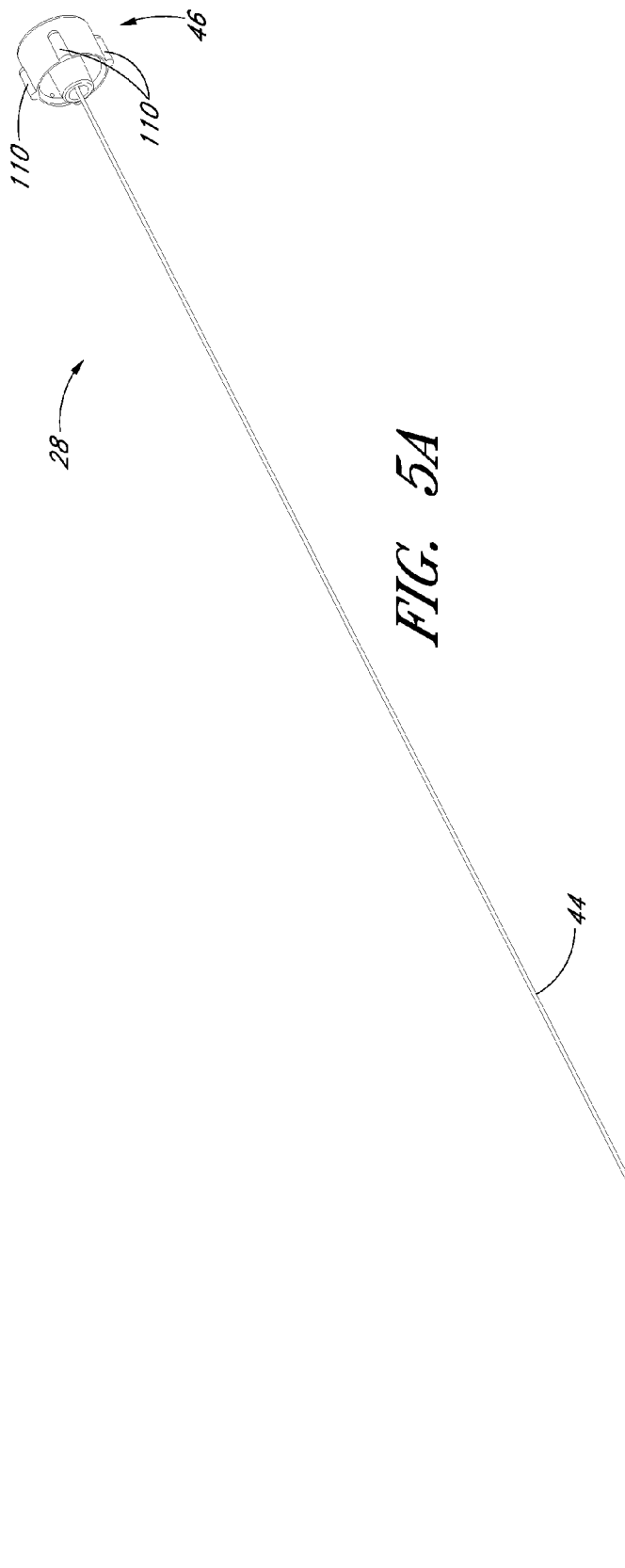
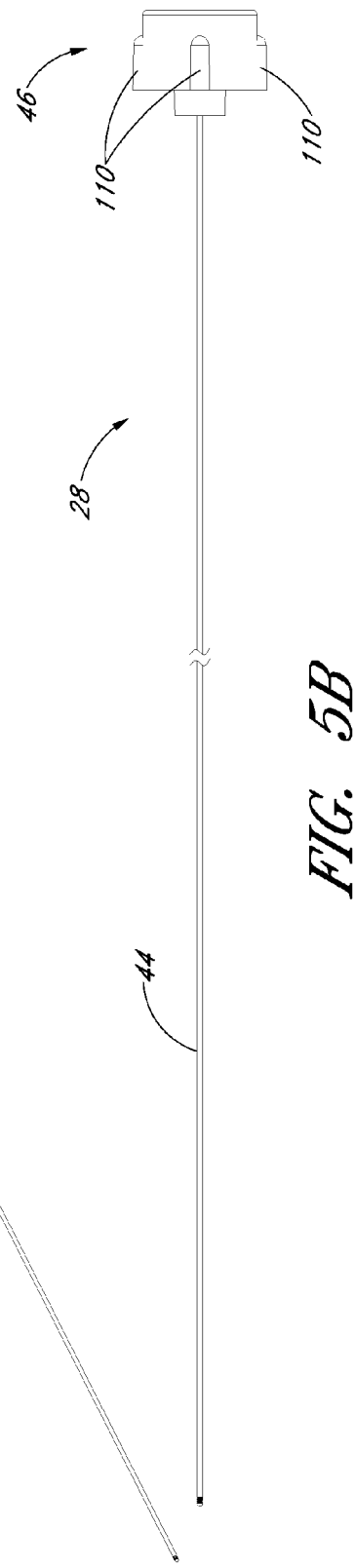
FIG. 5A
FIG. 5B

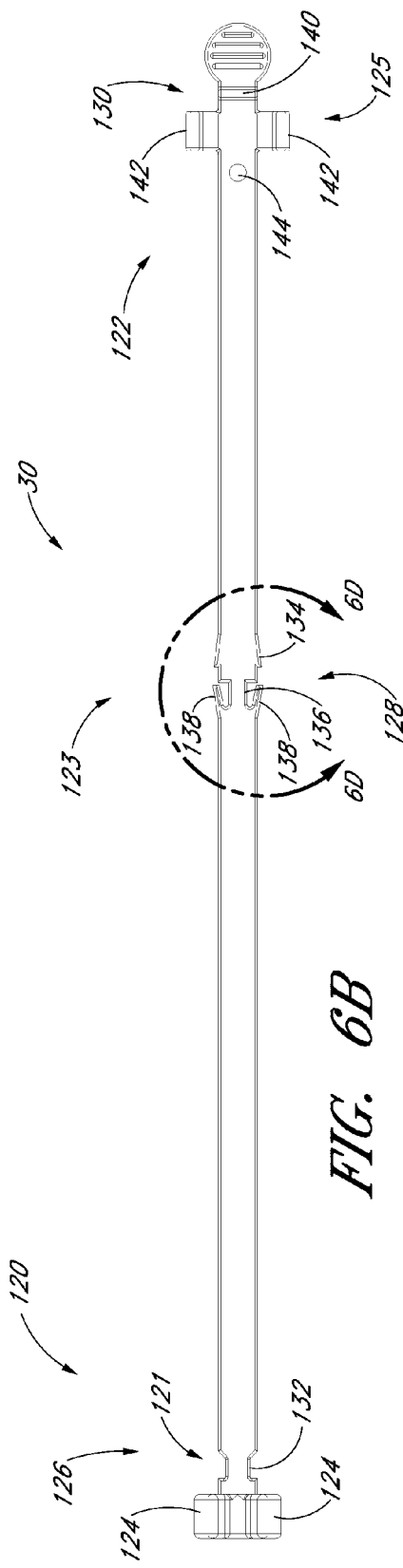
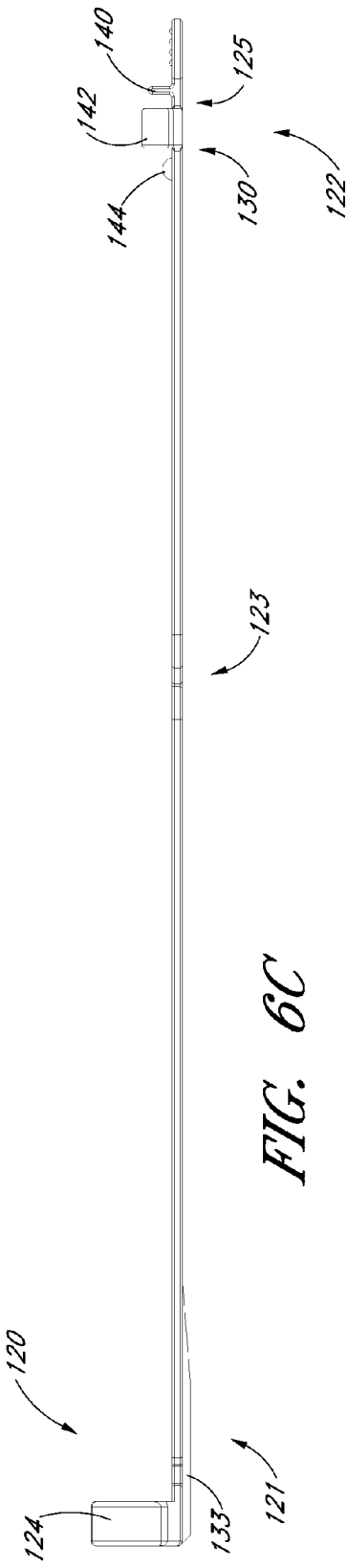
FIG. 6B
FIG. 6C

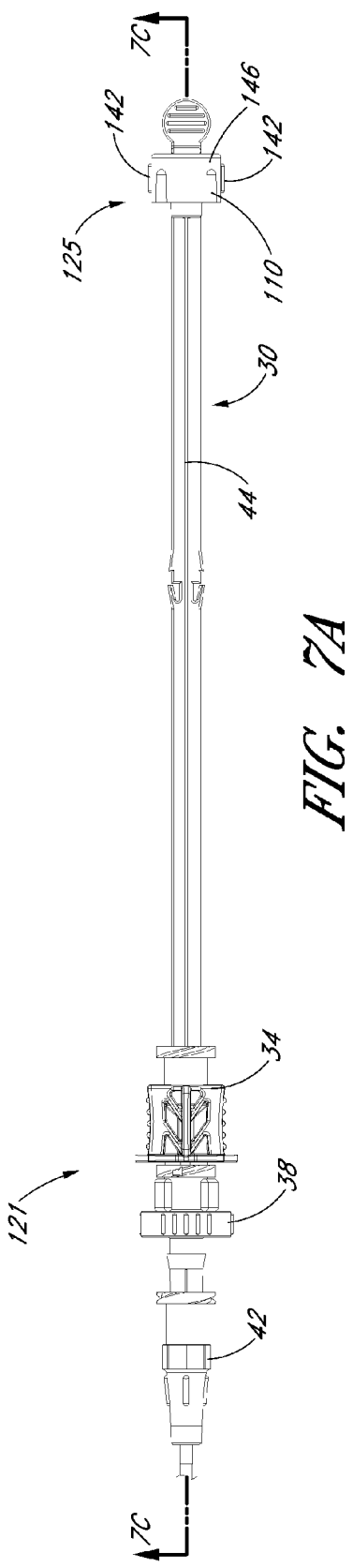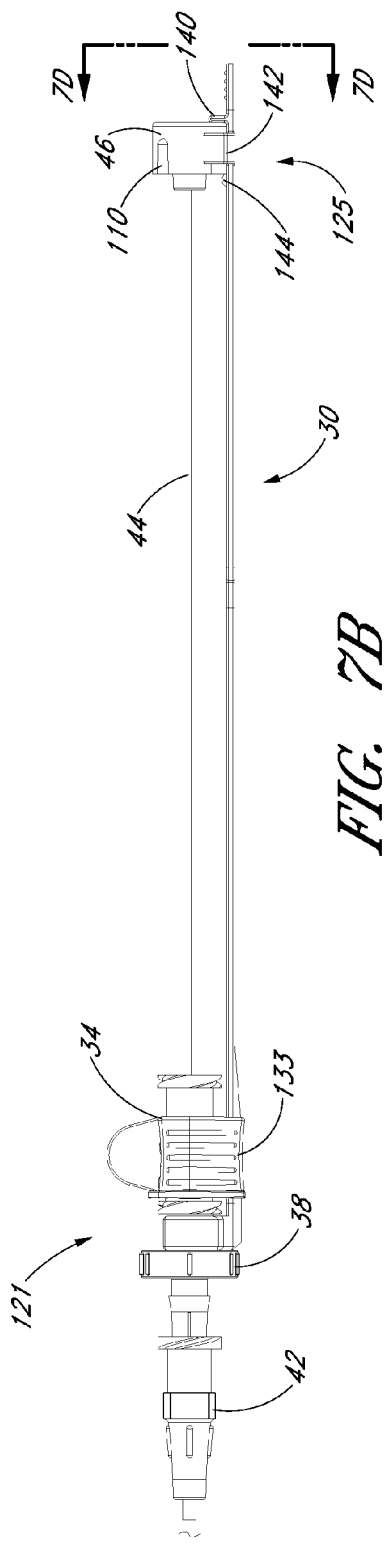
FIG. 7A
FIG. 7B

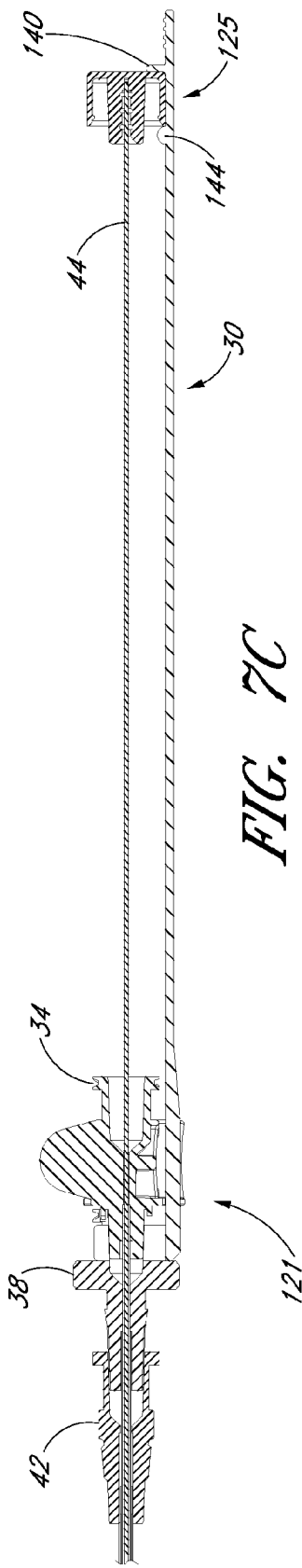
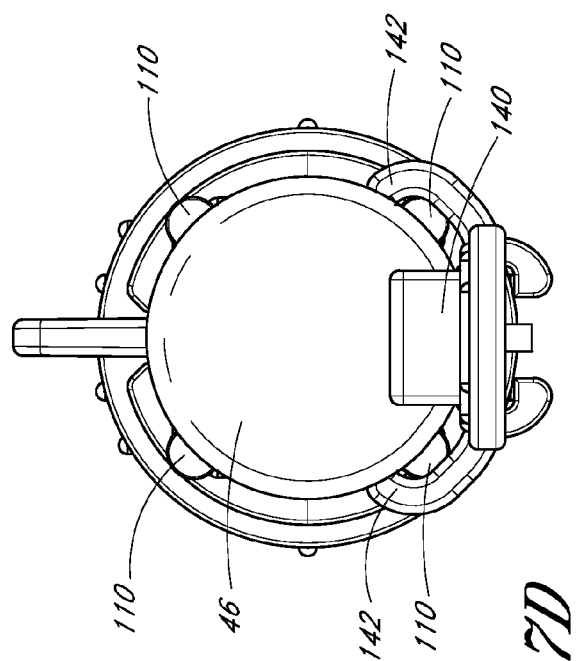
FIG. 7C
FIG. 7D

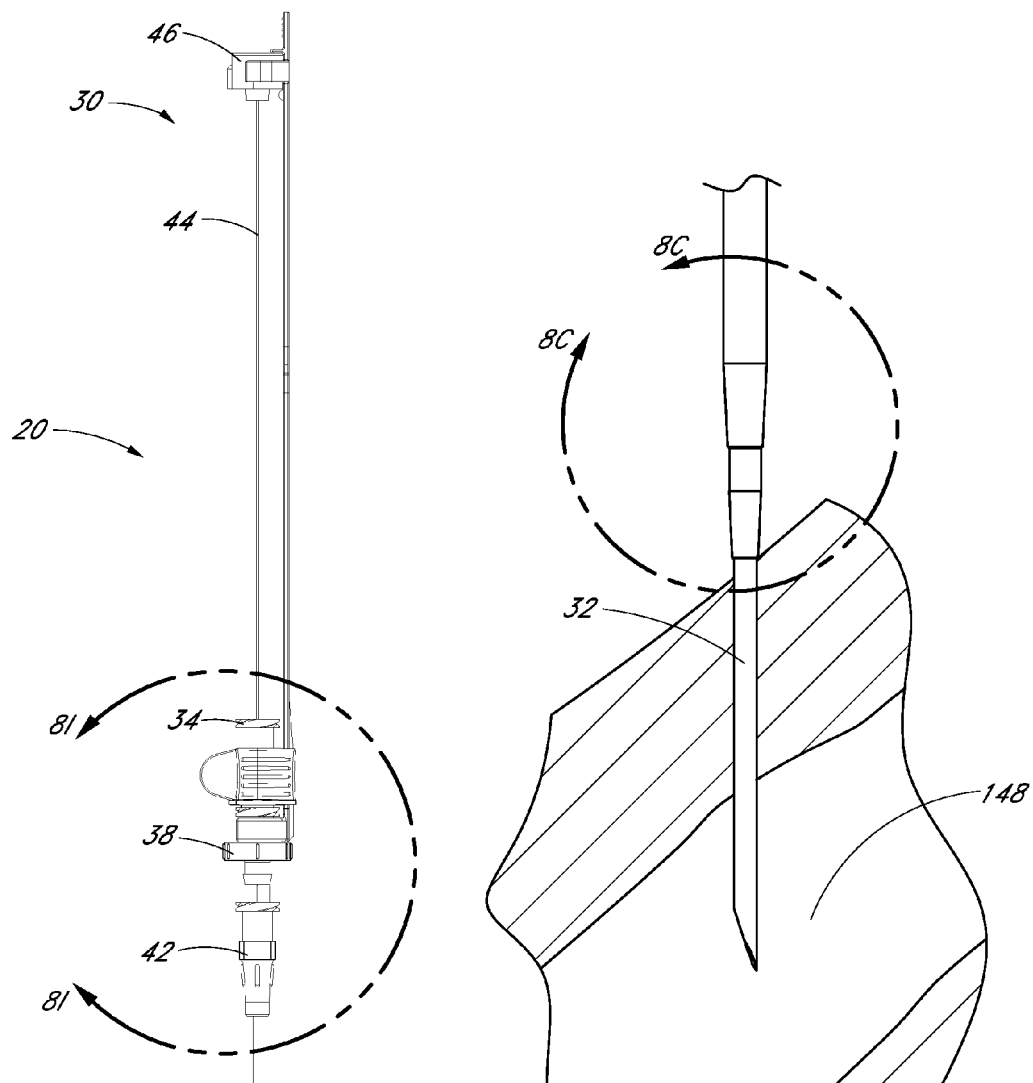
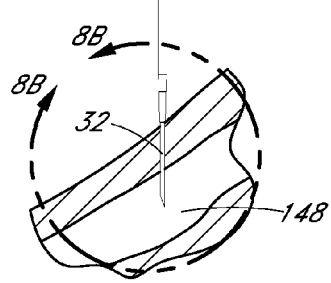
FIG. 8A
FIG. 8B

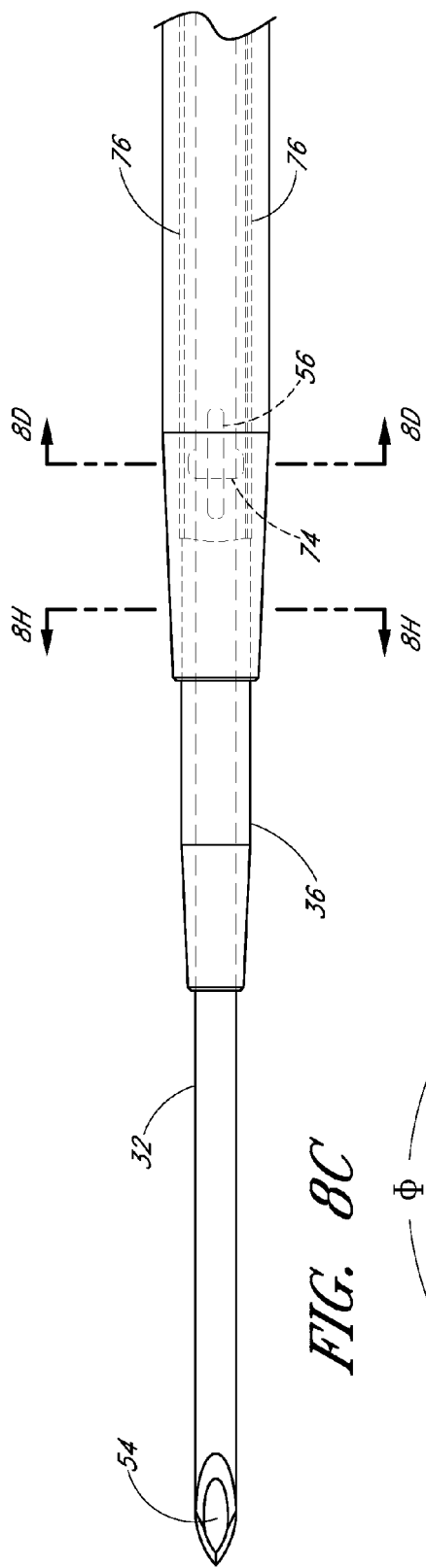
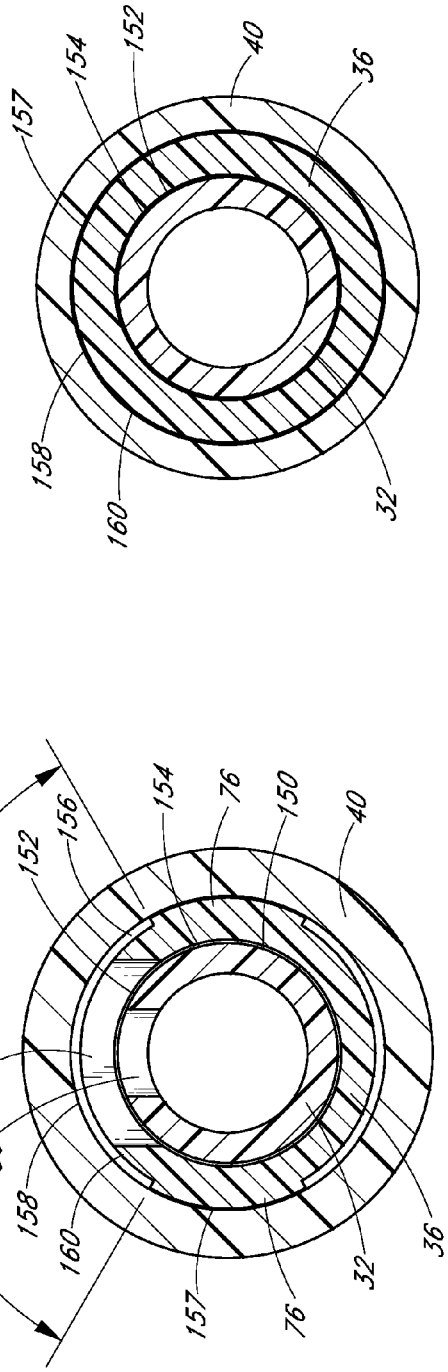
FIG. 8C
FIG. 8D
FIG. 8H

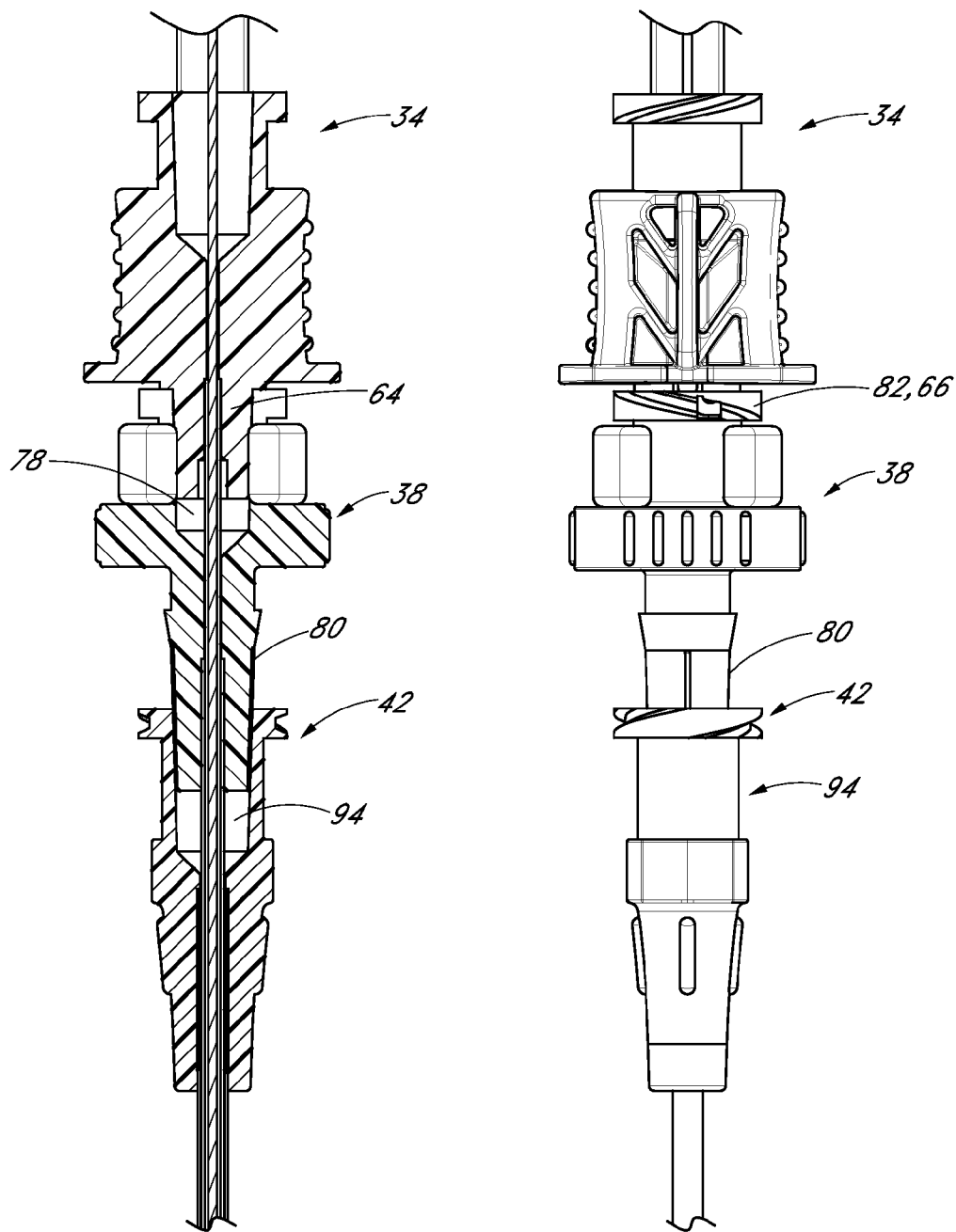

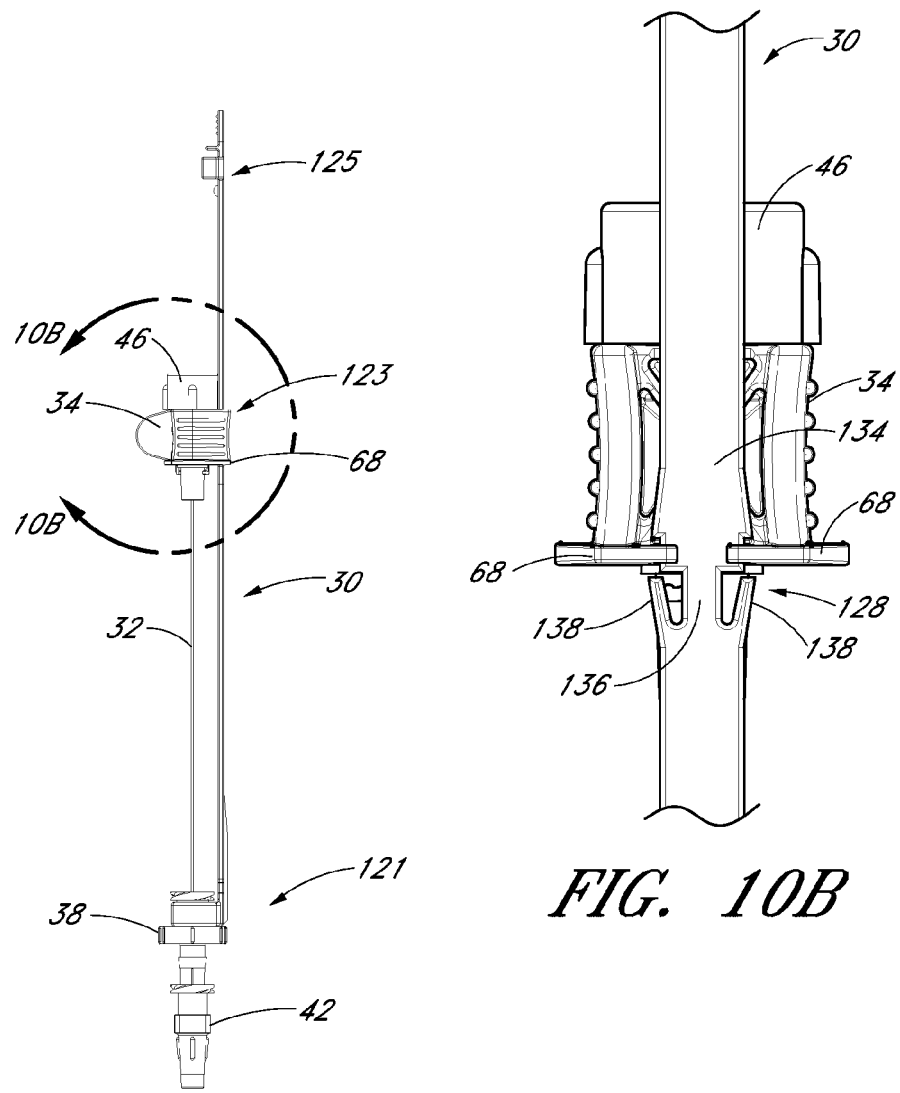
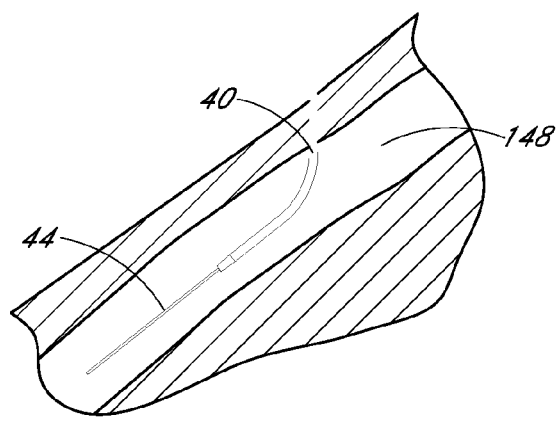
FIG. 10A
FIG. 10B

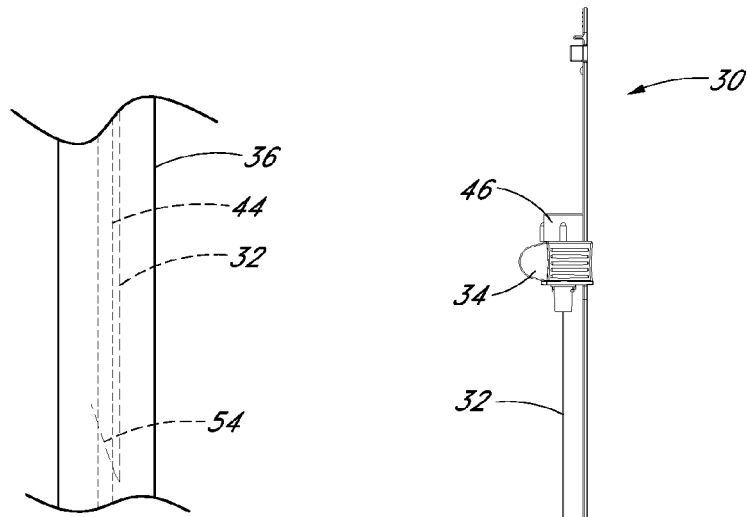
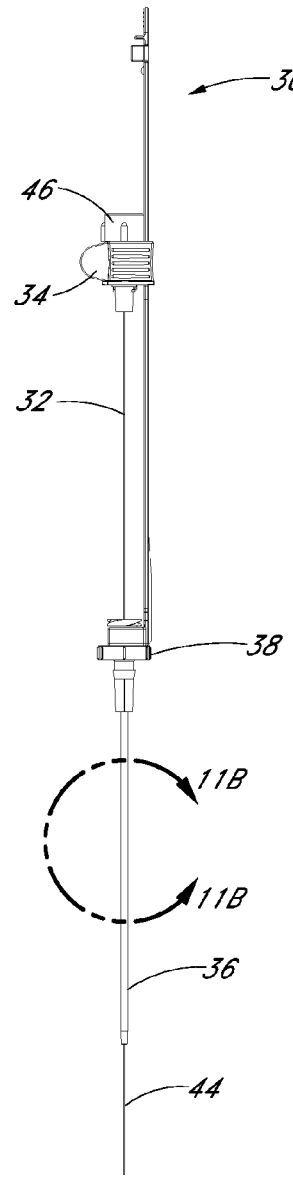
FIG. 11B
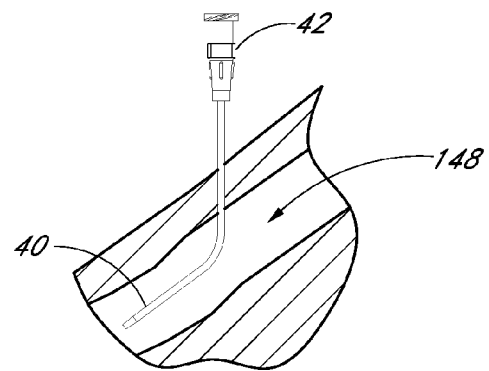
FIG. 11A

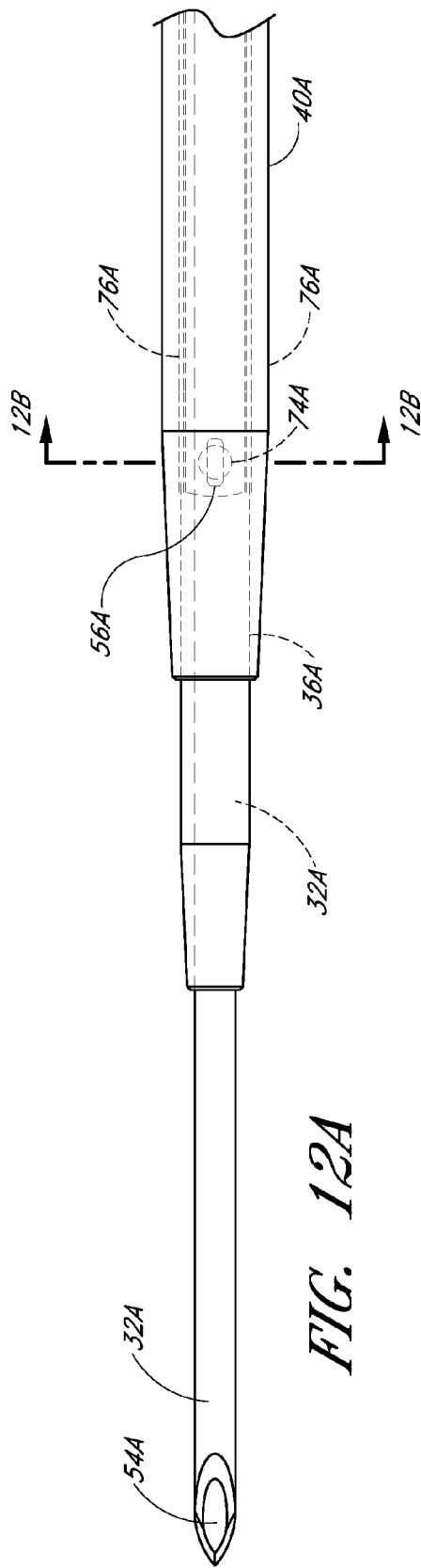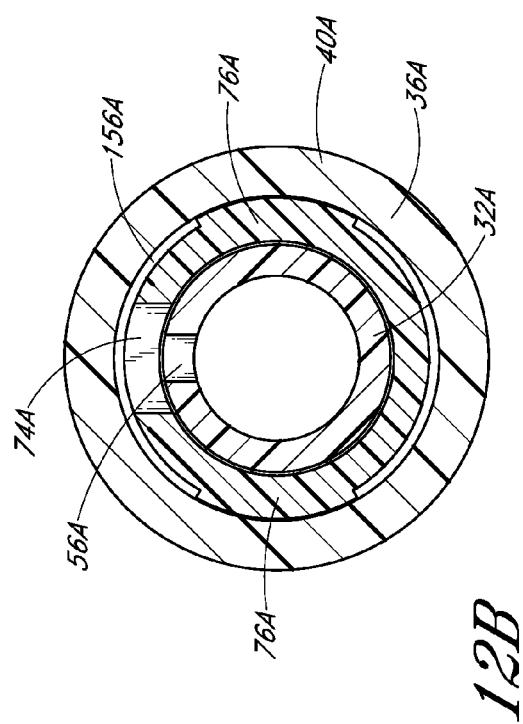

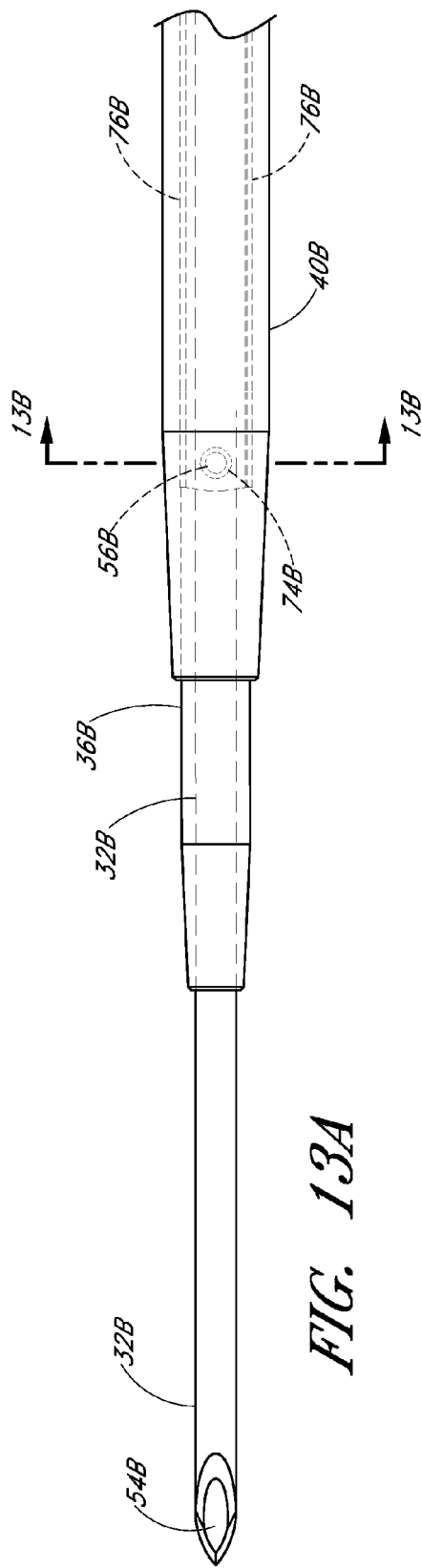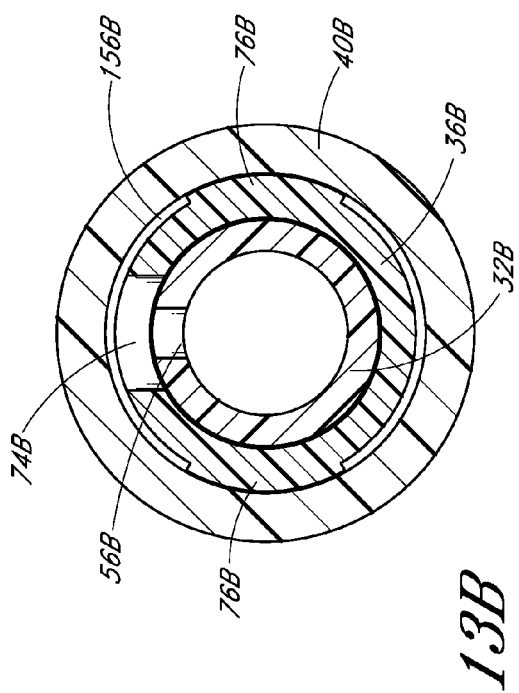
FIG. 13A
FIG. 13B

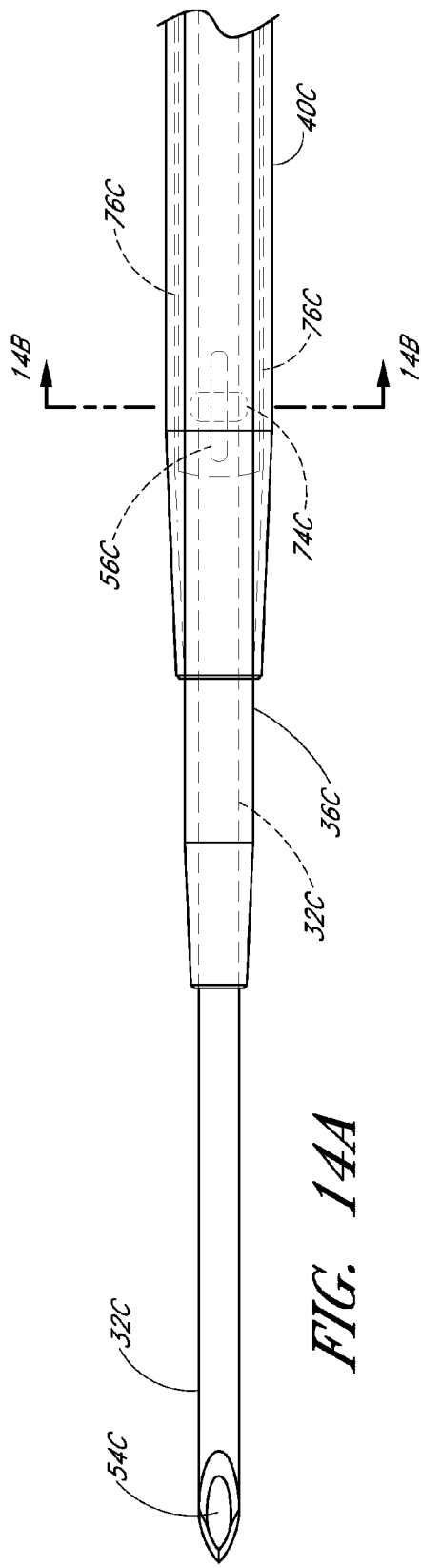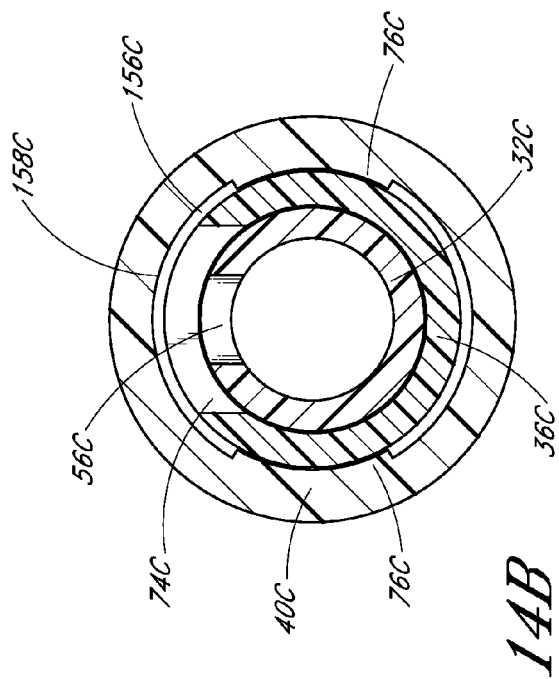
FIG. 14A
FIG. 14B

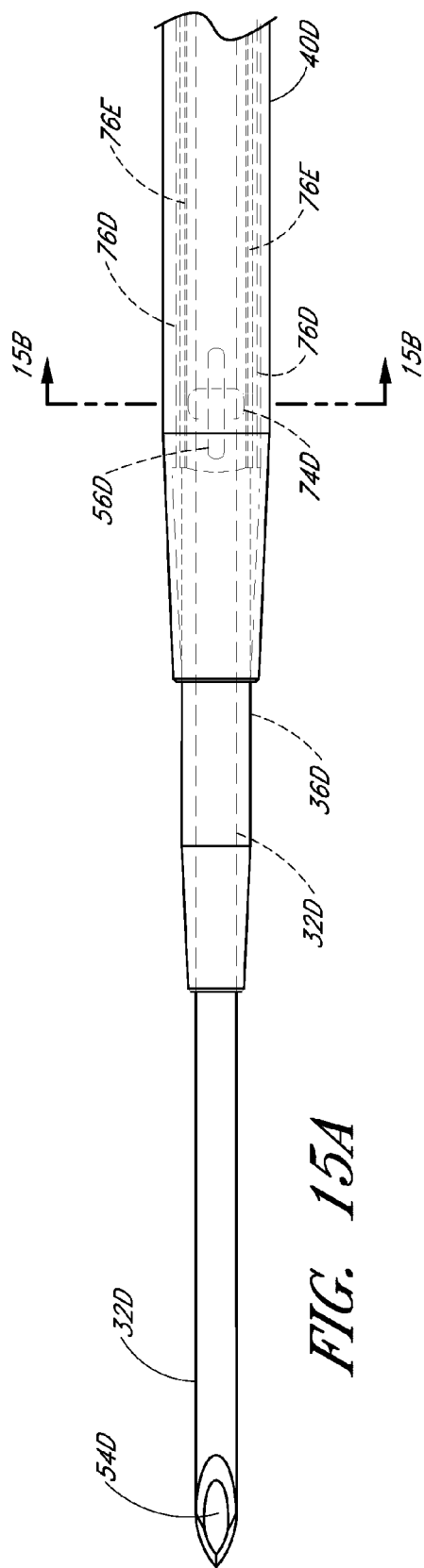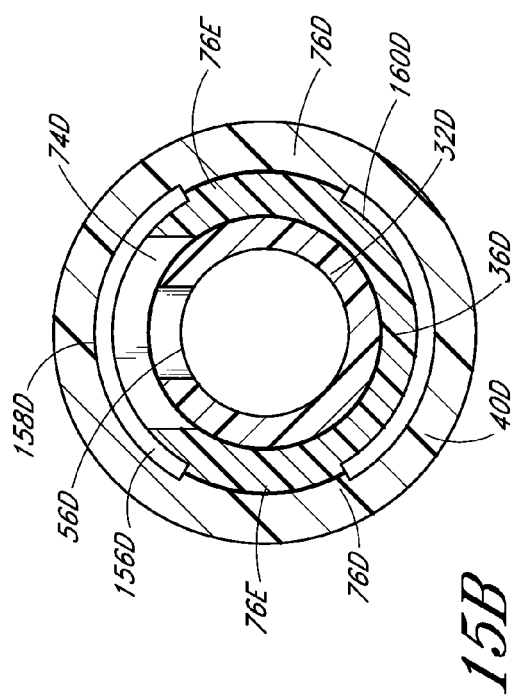

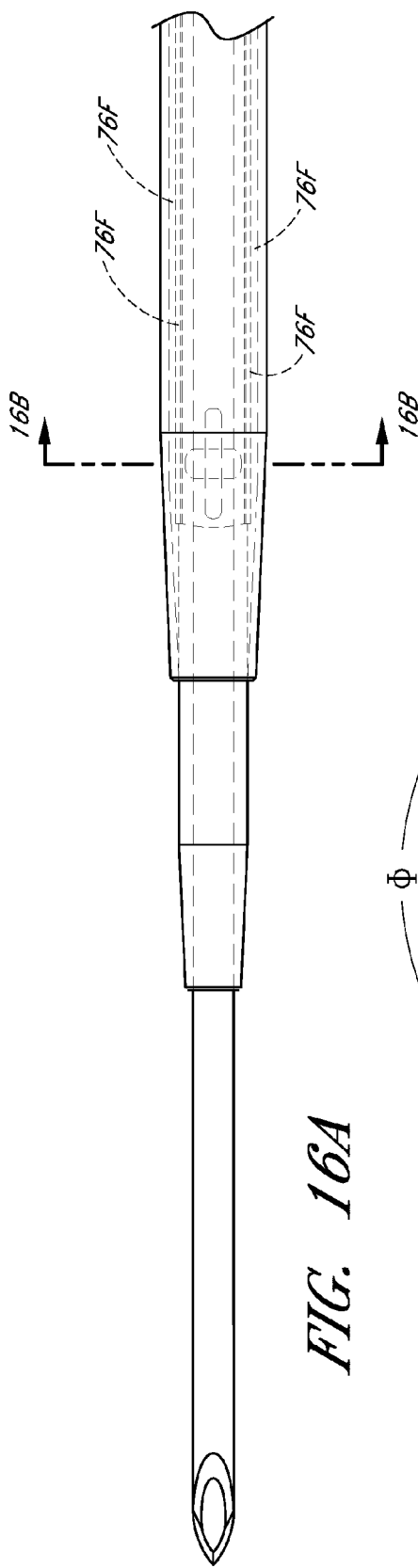
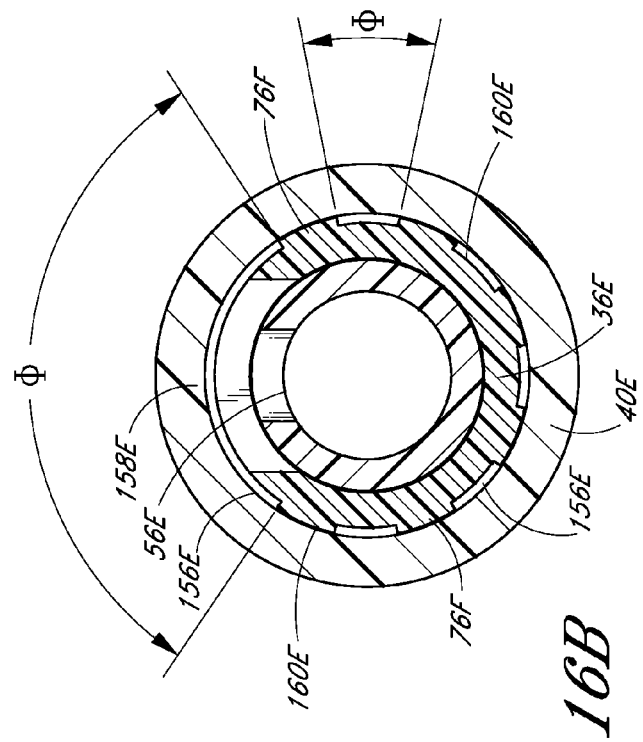
FIG. 16A
FIG. 16B

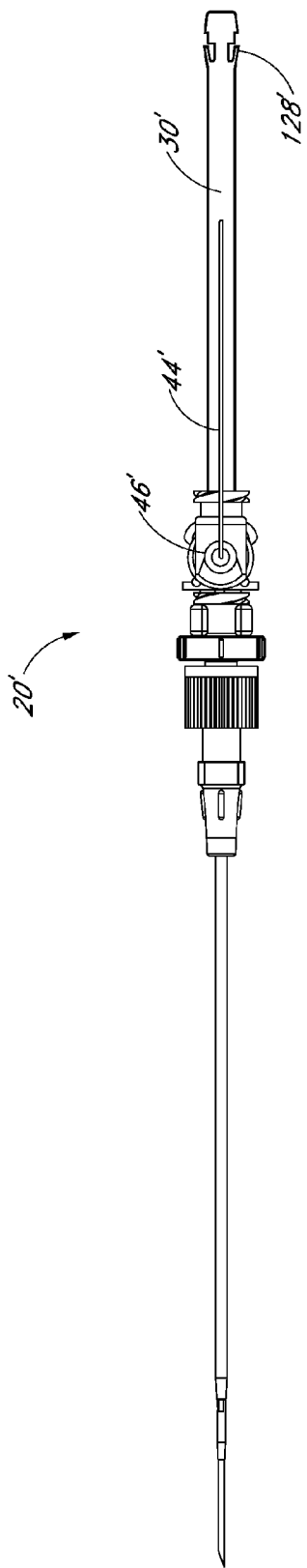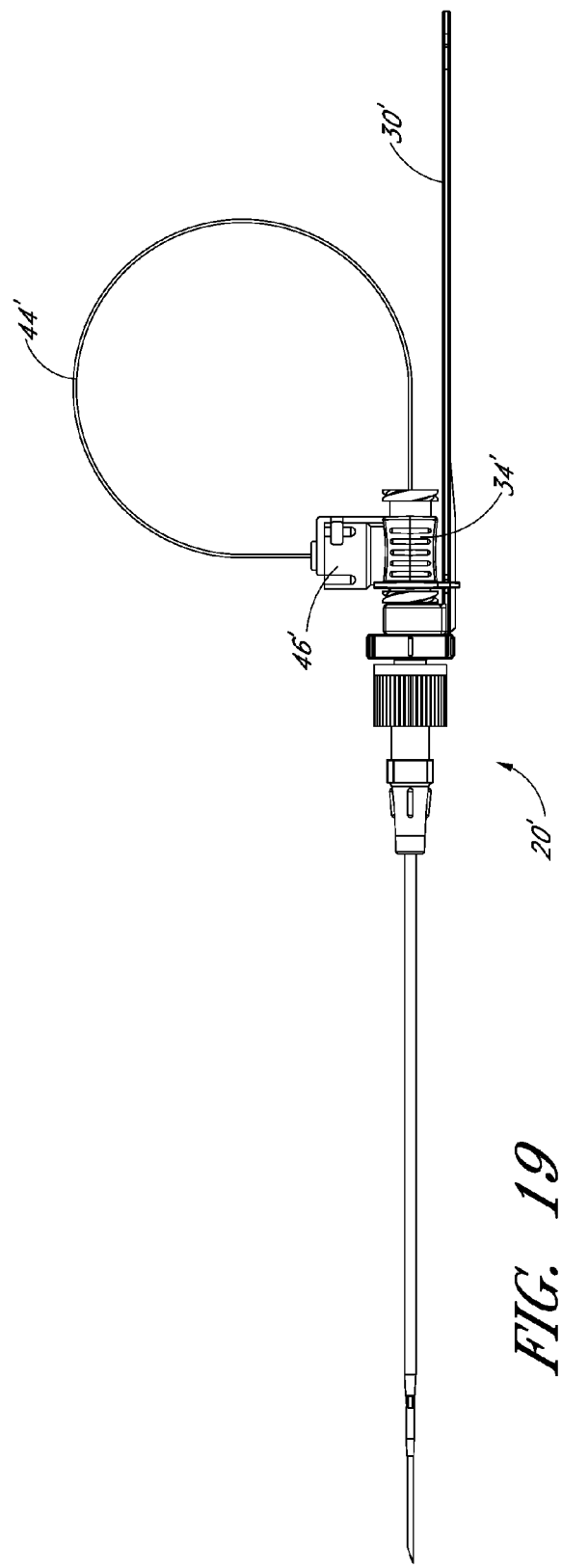

ACCESS DEVICE

CROSS-REFERENCE TO RELATED APPLICATIONS

This application is a continuation of U.S. patent application Ser. No. 12/922,373, filed Sep. 13, 2010, now issued as U.S. Pat. No. 8,202,251, which claims the benefit of International Application No. PCT/US09/37198, filed Mar. 13, 2009, which was published in English and designated the United States of America, and which further is related to and claims the benefit under 35 U.S.C. §119(e) to U.S. Provisional Patent Application Ser. Nos. 61/036,900 (filed Mar. 14, 2008) and 61/107,972 (filed Oct. 23, 2008), all of which are each hereby expressly incorporated by reference in their entirety.

BACKGROUND

1. Field

This invention is generally directed to access devices for introducing and/or delivering a medical article (such as, for example, a catheter, cannula, sheath, etc.) into a body space, such as, for example, an artery, vein, vessel, body cavity, or drainage site.

2. Description of the Related Art

A preferred non-surgical method for inserting a catheter or vascular sheath into a blood vessel involves the use of the Seldinger or a modified Seldinger technique, which includes an access needle that is inserted into a patient's blood vessel. A guidewire is inserted through the needle and into the vessel. The needle is removed, and a dilator and sheath in combination or separately are then inserted over the guidewire. The dilator and sheath, together or separately, are then inserted a short distance through the tissue into the vessel, after which the dilator and guidewire are removed and discarded. A catheter or other medical article may then be inserted through the sheath into the vessel to a desired location, or the sheath may simply be left in the vessel.

A number of vascular access devices are known. U.S. Pat. Nos. 4,241,019, 4,289,450, 4,756,230, 4,978,334, 5,124,544, 5,424,410, 5,312,355, 5,212,052, 5,558,132, 5,885,217, 6,120,460, 6,179,823, 6,210,332, 6,726,659 and 7,025,746 disclose examples of such devices. None of these devices, however, has the ease and safety of use that physicians and other healthcare providers would prefer. Thus, there exists a need for an easier-to-use and safer vascular access device, especially one that would clearly and promptly indicate when a blood vessel has been punctured and one that would reduce accidental needle sticks and other attendant risks of over-wire vascular access.

SUMMARY

Embodiments of the present invention involve several features for an access device useful for the delivery of a catheter or sheath into a space within a patient's body, such as, for example, a blood vessel or drainage site. Without limiting the scope of this invention, its more prominent features will be discussed briefly. After considering this discussion, and particularly after reading the Detailed Description of the Preferred Embodiments section below in combination with this section, one will understand how the features and aspects of these embodiments provide several advantages over prior access devices.

In one embodiment, an access device can place a medical article within a body space. The access device can include a needle with an elongated needle body. The elongated needle body can extend from a distal opening of a needle hub to its distal end. A first end of a guidewire can extend at least partially through the needle hub. The guidewire can also include a cap, at which the second end terminates. The needle hub and the cap can each have cooperating structure that engages together such that the first end of the guidewire can extend at least partially into the needle hub and the cap can releasably attach to a side of the needle hub.

In a similar embodiment, the needle hub and the can each have cooperating structure that engage together. The cooperating structure can allow the cap to releasably attach to the needle hub in at least two distinct positions.

In yet another embodiment, an access device for placing a medical article within a body space can be provided, comprising a needle and a guidewire. The needle can have an elongated body with a distal end and a hub. The hub can comprise a distal opening from which the needle body extends. The guidewire can have both first and second ends. The first end can extend at least partially into the needle hub and the guidewire can terminate at the second end. The needle hub and the guidewire can have a means for releasable attachment. The means can allow the first end of the guidewire to extend at least partially into the needle hub, and the second end to releasably attach to a side of the needle hub.

BRIEF DESCRIPTION OF THE DRAWINGS

These and other features, aspects, and advantages of the access device disclosed herein are described below with reference to the drawings of preferred embodiments, which are intended to illustrate and not to limit the invention. Additionally, from figure to figure, the same reference numerals have been used to designate the same components of an illustrated embodiment. Like components between the illustrated embodiments are similarly noted as the same reference numbers with a letter suffix to indicate another embodiment. The following is a brief description of each of the drawings.

FIG. 2A is a plan view of the needle from FIG. 1A and shows a fenestration near a distal end.

FIG. 2B is a side view of the needle from FIG. 1A and shows a fin near a proximal end.

FIG. 2E is an enlarged plan view of the needle hub of the needle of FIG. 2A.

FIG. 2F is an enlarged side view of the needle hub of the needle of FIG. 2A.

FIG. 2G is an enlarged proximal end view of the needle hub of the needle of FIG. 2A.

FIG. 3A is a plan view of the dilator from FIG. 1A and shows a fenestration near a distal end. FIG. 3A also shows longitudinally arranged grooves in the luer surface for venting air from between the dilator and sheath.

FIG. 3B is a cross-sectional view taken along the lines 3B-3B in FIG. 3A.

FIG. 3C is an enlarged plan view of a portion of the dilator from FIG. 3A and shows the fenestration and longitudinal channel.

FIG. 3D is an enlarged end view of the dilator hub from FIG. 3A.

FIG. 3E is a perspective view of another embodiment of the dilator hub that includes a locking spin nut configured to secure to a sheath that has a corresponding screw thread.

FIG. 3F is a cross-sectional view taken along the lines 3F-3F in FIG. 3A and shows the grooves equally spaced about the circumference of the luer surface.

FIG. 5A is a perspective view of the guidewire section from FIG. 1A and shows a guidewire hub connected to a proximal end of a guidewire.

FIG. 5B is a plan view of the guidewire section of the embodiment depicted in FIG. 5A.

FIG. 6B is a plan view of the track in FIG. 6A and shows a locking mechanism for locking the needle relative to the dilator.

FIG. 6C is a side view of the track in FIG. 6B.

FIG. 7A is a plan view of the access device from FIG. 1A and shows the locking mechanism from FIG. 6E with the guidewire section locked to the track in the pre-loaded state.

FIG. 7B is a side view of the access device and locking mechanism from FIG. 7A.

FIG. 7C is a cross-sectional view through the access device of FIG. 7A and shows the guidewire hub disposed between an element and stop of the track.

FIG. 7D is an enlarged end view of the access device from FIG. 7B and shows two arms extending from the track and around at least a portion of the guidewire hub.

FIG. 8A is a plan view of the embodiment depicted in FIG. 1A illustrating the insertion of the distal end of the access device into a patient.

FIG. 8B is an enlarged view of the embodiment depicted in FIG. 8A focusing on the area of the access device adjacent to the patient.

FIG. 8C is an enlarged view of a portion of the embodiment depicted in FIG. 8B and illustrates the needle opening or fenestration aligned with the dilator opening or fenestration in hidden lines.

FIG. 8D is an enlarged cross-sectional view of a portion of the embodiment depicted in FIG. 8C and shows the needle opening or fenestration aligned with the dilator opening or fenestration so as to allow fluid to flow from inside the needle to a channel formed between the sheath and dilator.

FIG. 8H is an enlarged cross-sectional view of a portion of the embodiment depicted in FIG. 8C taken through a region distal of the channel in the dilator.

FIG. 8I is an enlarged view of the embodiment depicted in FIG. 8A focusing on the area where the needle hub is locked to the dilator hub when the needle hub is in the first position.

FIG. 8J is a cross-sectional view of the embodiment depicted in FIG. 8I.

FIG. 10A is a side view of the embodiment depicted in FIG. 1A illustrating the dilator and sheath being advanced distally relative to the needle body from the position illustrated in FIG. 9A.

FIG. 10B is an enlarged rear view of the embodiment depicted in FIG. 10A focusing on the area where the needle hub is locked to the track when the needle hub is in the second position.

FIG. 11A is a side view of the embodiment depicted in FIG. 1A illustrating the removal of the guidewire, needle body, and dilator from the sheath.

FIG. 11B is an enlarged view of the portion of the embodiment illustrated in FIG. 11A showing the needle tip covered by the dilator during removal of the guidewire, needle body, and dilator from the sheath.

FIG. 12A is an enlarged plan view that illustrates another embodiment of the aligned openings or fenestrations in the needle and dilator.

FIG. 12B is an enlarged cross-sectional view along lines 13B-13B in FIG. 12A and shows the needle opening or fenestration aligned with the dilator opening or fenestration so as to allow fluid to flow from inside the needle to a channel formed between the sheath and dilator.

FIG. 13A is an enlarged plan view that illustrates another embodiment of the aligned openings or fenestrations in the needle and dilator.

FIG. 13B is an enlarged cross-sectional view along lines 13B-13B in FIG. 13A and shows the needle opening or fenestration aligned with the dilator opening or fenestration so as to allow fluid to flow from inside the needle to a channel formed between the sheath and dilator FIG. 14A is an enlarged plan view that illustrates another embodiment of the channel formed between the dilator and the sheath.

FIG. 14B is a cross-sectional view along lines 14B-14B in FIG. 14A and shows the thickness of the channel extending into the sheath.

FIG. 15A is an enlarged plan view that illustrates another embodiment of the channel formed between the dilator and the sheath.

FIG. 15B is a cross-sectional view along lines 15B-15B in FIG. 15A and shows the thickness of the channel extending into both the dilator and the sheath.

FIG. 16A is an enlarged plan view that illustrates another embodiment of the channel formed between the dilator and the sheath.

FIG. 16B is a cross-sectional view along lines 16B-16B in FIG. 15A and shows a plurality of equally spaced channels in the form of splines extending into the dilator.

FIG. 18 is a plan view of another embodiment of an access device in an attached position.

FIG. 19 is a side view of the access device of FIG. 18.

DETAILED DESCRIPTION

Figure 1A:
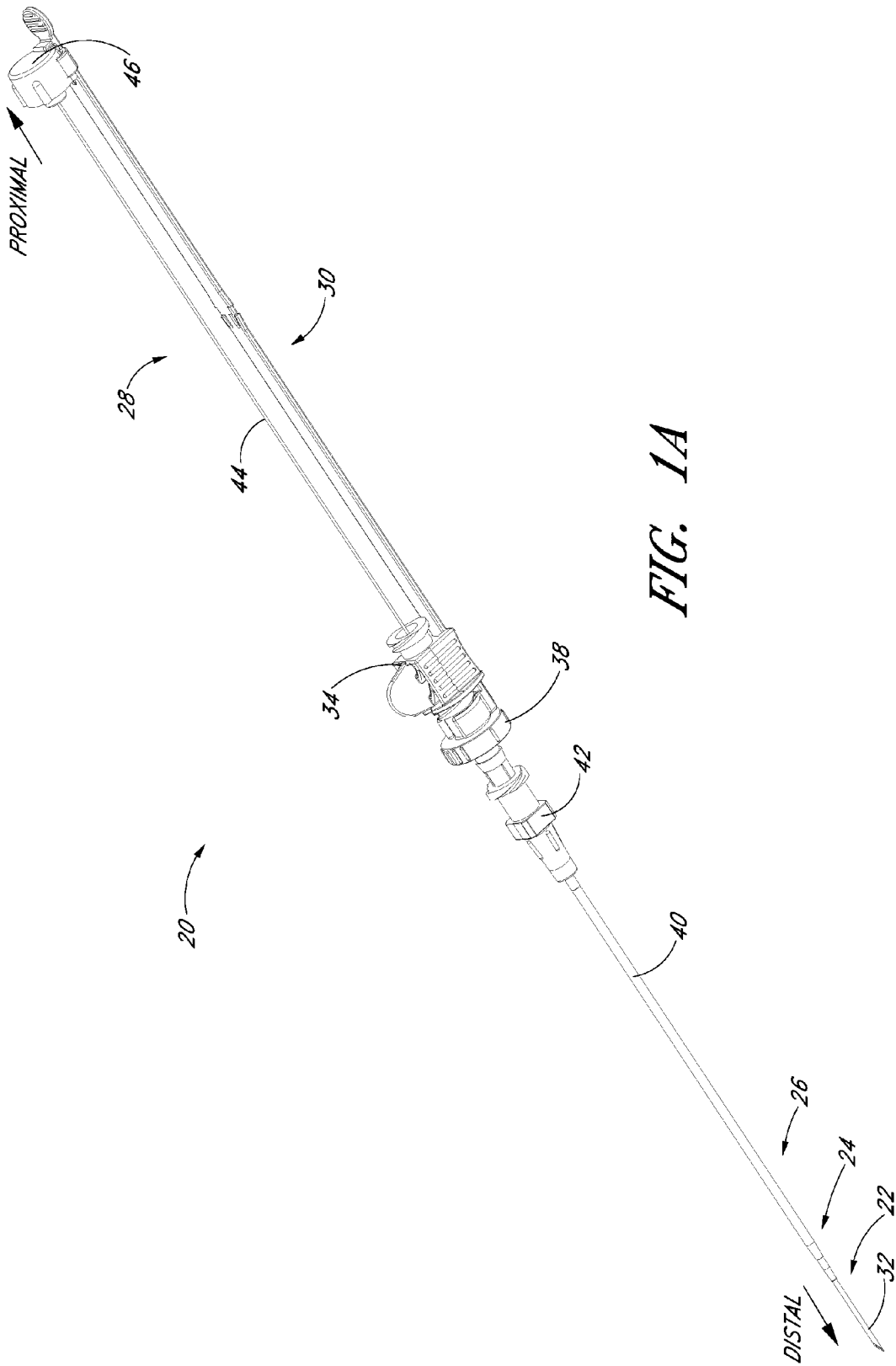
FIG. 1A is a perspective view of a preferred embodiment of an access device configured in accordance with the present invention and shows a pre-loaded guidewire section coaxially aligned with a needle, a dilator, and a medical article.

The present disclosure provides an access device for the delivery of a medical article (e.g., catheter or sheath) to a blood vessel or drainage site. FIG. 1A illustrates an access device 20 that is configured to be inserted into a blood vessel (e.g., a vein or an artery) in accordance with a preferred embodiment of the present invention. While the access device is described below in this context (i.e., for vascular access), the access device also can be used to access and place a medical article (e.g., catheter or sheath) into other locations within a patient's body (e.g., a drainage site) and for other purposes (e.g., for draining an abscess).

The present embodiment of the access device is disclosed in the context of placing an exemplary single-piece, tubular medical article into a body space within a patient. Once placed, the tubular article can then be used to receive other medical articles (e.g., catheters, guidewires, etc.) to provide access into the body space and/or be used to provide a passage way for introducing fluids into the body space or removing (e.g., draining) fluids from the body space. In the illustrated embodiment, the tubular medical article is a sheath or catheter that is configured primarily to provide a fluid passage into a vein. The principles of the present invention, however, are not limited to the placement of single piece sheaths or catheters, or to the subsequent insertion of a medical article via the sheath or catheter. Instead, it will be understood by one of skill in this art, in light of the present disclosure, that the access device disclosed herein also can be successfully utilized in connection with placing one or more other types of medical articles, including other types of sheaths, fluid drainage and delivery tubes, and single or multi-lumen catheters directly in the patient or indirectly via another medical article.

For example, but without limitation, the access device disclosed herein can also be configured to directly or indirectly place central venous catheters, peripherally inserted central catheters, hemodialysis catheters, surgical drainage tubes, tear-away sheaths, multi-piece sheaths, scopes, as well as electrical conduit for wires or cables connected to external or implanted electronic devices or sensors. As explained above, the medical articles listed above may be directly placed in the patient via the dilator, needle, and guidewire of the access device or subsequently placed within the patient via a medical article that was placed within the patient via the dilator, needle, and guidewire of the access device.

Further, the embodiments disclosed herein are not limited to co-axial insertion of a single medical article. For example, two catheters may be inserted in the patient via an inserted sheath or a second catheter may be inserted in the patient via an inserted first catheter. Further, in addition to providing a conduit into the vessel or other body space, the medical article inserted via the dilator, needle, and guidewire can form a lumen that is in addition to the lumen(s) of the subsequently inserted medical article. One skilled in the art can also find additional applications for the devices and systems disclosed herein. Thus, the illustration and description of the access device in connection with a sheath (e.g., for micro puncture applications) is merely exemplary of one possible application of the access device.

Figure 1B:
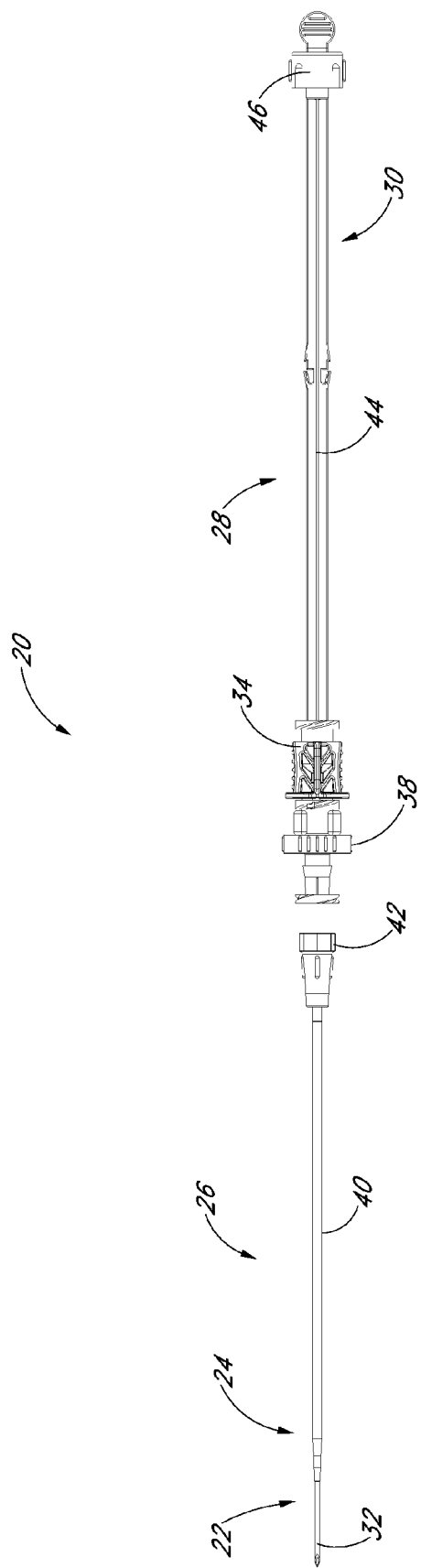
FIG. 1B is a plan view of the embodiment depicted in FIG. 1A.

FIGS. 1A and 1B illustrated a preferred embodiment of an access device 20. The access device 20 comprises a needle 22, a dilator 24, and a sheath 26. In the illustrated embodiment, the access device also includes a guidewire section 28 and a track 30. As best seen in FIG. 1B, the dilator 24 is preferably coaxially mounted on the needle 22, and the sheath 26 is coaxially mounted on the dilator 24. The telescoping nature of the access device's components can also be accomplished by arranging the components with their axes arranged substantially parallel rather than coaxially (e.g., a monorail-type design).

Each of these components includes a luminal fitting at a terminal end or transition (i.e., a hub) and elongated structure that extends from the fitting. Thus, in the illustrated embodiment, the needle 22 includes a needle body 32 that extends distally from the needle hub 34, the dilator 24 includes a dilator shaft 36 that extends distally from a dilator hub 38, and the sheath 26 includes a sheath body 40 that extends distally from a sheath hub 42. The guidewire section 28 comprises a guidewire 44 and preferably a guidewire hub or cap 46. In the illustrated embodiment, the guidewire hub 46 is disposed on the proximal end of the guidewire 44; however, in other applications, the hub 46 can be disposed at a location between the ends of the guidewire 44.

Figure 2C:
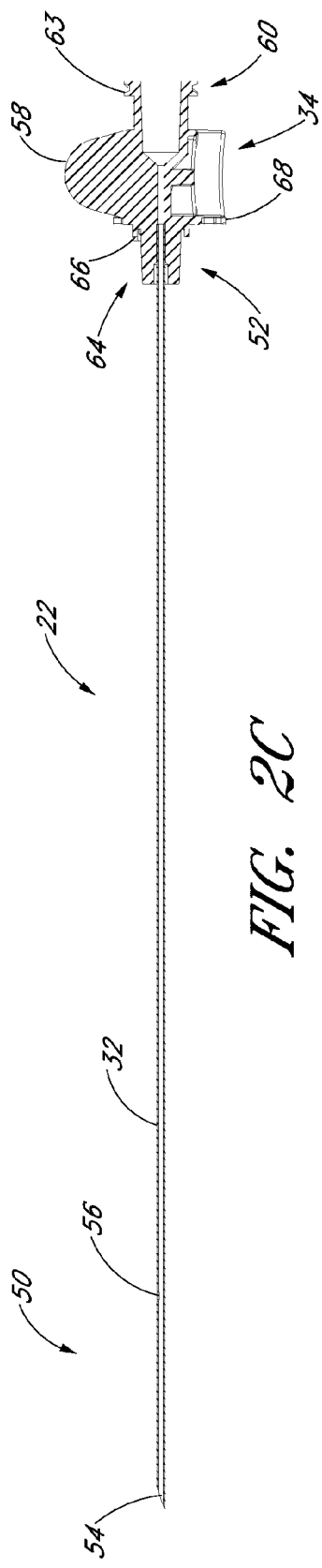
FIG. 2C is a cross-sectional view taken along the lines 2C-2C in FIG. 2A.

FIGS. 2A-2G illustrate the needle body 32 and needle hub 34 of the needle 22, which are configured in accordance with a preferred embodiment of the access device, in isolation from the other components of the access device 20. As best seen in FIGS. 2A and 2B, the needle hub 34 is disposed on a proximal end of the needle body 32. The needle body 32 terminates at a distal end near a distal portion 50 of the needle 22, and the needle hub 34 lies at a proximal portion 52 of the needle 22.

The needle body 32 preferably has an elongated tubular shape having a circular, constant-diameter inner bore and a circular, constant-diameter exterior surface. In other embodiments, however, the needle body 32 can have other bore and exterior shapes (such as, for example, but without limitation, an oval cross-sectional shape). The interior or exterior of the needle can also include grooves or channels. The grooves or channels may guide fluids within the needle bore either around or to certain structures of the needle 22 or within the needle 22 (e.g., around the guidewire). In some embodiments, the grooves or channels may assist in maintaining a desired orientation of the needle 22 with respect to the dilator.

The needle body 32 has a sufficiently long length to access a targeted subcutaneous body space and has a sufficient gauge size to withstand the insertion forces when accessing the body space without causing undue trauma. For many applications, the needle body can have a length between 3-20 cm, and more preferably between 3-10 cm. For example, to access a body space (e.g., a vessel) in the thorax of an adult human, the needle body 32 preferably has a length of 7 cm or greater, and more preferably has a length of 9 cm or greater, and most preferably has a length of 9 to 10 cm. The size of the needle preferably is 18 gauge or smaller, and more preferably between 18-28 gauge, and most preferably between 18-26 gauge for micro-puncture applications (peripheral IVs). For applications with a neonate, the length and gauge of the needle body 32 should be significantly shorter and smaller, for example preferably between 3-4 cm and between 26-28 gauge.

Figure 2D:
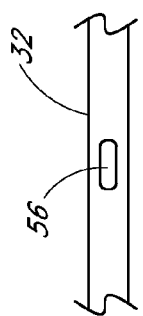
FIG. 2D is an enlarged plan view of a portion of the needle of FIG. 2A and shows the fenestration.

As best seen in FIGS. 2A and 2D, the needle body 32 includes at least one fenestration or opening 56 near a distal end of the needle body 32. The fenestration 56 extends through the wall of the needle body 32 and can have a variety of shapes and orientations on the needle body 32, as described in detail below. In addition, the needle body 32 can have a bevel tip 54 disposed on the distal portion 50.

As is illustrated in FIGS. 2A, 2B, a fin 58 is preferably disposed at a circumferential location around the needle hub 34 that is aligned with the circumferential locations of the bevel on the needle tip and the opening or fenestration 56 in the needle. That is, the fin 58 is indexed with the bevel and fenestration. During use, the physician or healthcare provider can determine the orientation of the beveled needle tip (and the fenestration 56) by noting the orientation of the exposed fin 58 even though the bevel is inside the vessel and the fenestration is covered by the sheath and/or dilator. For example, in the illustrated embodiment, an orientation of the fin 58 away from the patient coincides with a bevel up orientation of the needle tip within the vessel. The fenestration 56 is also on the same side as the fin 58, as seen in FIG. 2C.

The fin 58 also provides a grasping region to manipulate the needle hub 34. For example, a physician or healthcare provider can place an index finger and thumb on the sides of the fin 58 to stabilize the needle hub 34, relative to the dilator 24 and/or sheath 26. In the illustrated embodiment, as the dilator/sheath slides distally over the needle, the needle hub 34 slides relatively along the track 30 between a first position 121 and a second position 123 (example portions illustrated in FIG. 6A). The fin 58 can be held when performing the insertion step (which will be described below). In addition, the fin 58 can be used to stabilize the needle hub 34 while rotating the dilator hub 38. Furthermore, the fin 58 can be used by a physician or healthcare provider as an aid to grasp the access device 20 when the needle hub 34 is disposed at any position along the track 30.

FIG. 2D is an enlarged view of the side opening or fenestration 56 in the needle body 32. The one or more fenestration 56 provides a path through the side of the needle body 32. The fenestration 56 illustrated in FIG. 2D has an oblong shape. The shape of the side opening 56, however, is not limited to the illustrated embodiment and may be round, oblong, square, or another shape.

With specific reference now to FIGS. 2E-2G, the needle hub 34 preferably includes locking structures at the proximal portion and distal portion of the needle hub 34. These locking structures may be a luer-thread-type or another type of connections.

The locking structure on the proximal portion 52 of the needle hub 34 allows the physician or healthcare provider to secure another medical article to the proximal end of the needle hub 34. For example, the needle hub 34 in the illustrated embodiment includes an annular flange or lip 63. The lip 63 is threaded to allow the needle hub 34 to attach to other medical articles with a corresponding luer-nut locking feature. Additionally, a physician or healthcare provider may attach a syringe or monitoring equipment to the locking structure on the proximal end to perform other procedures as desired. The needle hub 34 can also include a septum at its proximal end and/or a side port if these features are desirably for a particular application.

The locking structure on the distal portion of the needle hub 34 allows the physician or healthcare provider, for example, to lock the needle hub 34 to the dilator hub 38 when the needle hub 34 is in the first position 121. In the illustrated embodiment, the locking structure includes a latch element 66 on the needle hub 34. The latch element 66 releasably locks the needle hub 34 to the dilator hub 38. The locking structure allows the healthcare provider to advance the needle into a patient while grasping the needle hub 34, the dilator hub 38 or both.

As explained below in greater detail, the guidewire 44 is introduced through a hollow portion 62 of the needle hub 34, through the needle body 32, and into a punctured vessel. The guidewire 44 allows the healthcare provider to guide the dilator 24 and sheath 26 into the vessel.

The needle hub 34 may also comprise two tangs 68 that allow the needle hub 34 to slide along the track 30 between a first position 121 and a second position 123. While in the preferred embodiment the two tangs 68 of the needle hub 34 are engaged with the track 30 between the first position 121 and the second position 123, in other embodiments the needle hub 34 is only engaged with the track 30 over a portion of the length of the track 30 between the first position 121 and the second position 123. The sliding interconnection between the track 30 and the needle hub 34 also can be accomplished using other cooperating structures (e.g., a corresponding pin and tail of dovetail connection).

FIG. 3A is a plan view of the dilator 24 of the embodiment depicted in FIG. 1A. FIG. 3B is a cross-sectional view of the dilator 24 of the embodiment depicted in FIG. 3A, taken along line 3B-3B. As shown in FIGS. 3A and 3B, the illustrated dilator 24 comprises a dilator shaft 36, a dilator hub 38, a distal region 70, and a proximal region 72. In the illustrated embodiment, the dilator shaft 36 includes a side openings or fenestrations 74; however, in other embodiments, the dilator shaft 36 can include fewer or greater numbers of fenestrations 74. For example, the dilator shaft 36 may not include a fenestration 74 where a blood flash chamber(s) is disposed within the dilator (as will be described in more detail below).

The dilator hub 38 may comprise one or more vents. In the illustrated embodiments, the vents in the dilator hub 38 are formed by grooves 75. Additionally, the dilator shaft 36 may comprise one or more longitudinal channels formed in the outer surface of the dilator shaft 36. In the illustrated embodiment, the channel is an open channel. The side walls of the open channel are formed by ridges 76. In the illustrated embodiment, the ridges 76 define generally smooth, arcuate exterior surfaces that interface with the sheath 26; however, in other embodiments, the ridges can have other shapes (e.g., can define more pronounced apexes). Once assembled within a sheath body 40, the open channel in the dilator shaft 36 is closed by the inside diameter of the sheath body 40.

FIG. 3C is an enlarged plan view of a portion of the embodiment illustrated in FIG. 3A. As noted above, the illustrated dilator shaft 36 comprises one or more side openings 74 and one or more channels formed between ridges 76. The side opening or fenestration 74 provides a fluid path through the side of the dilator shaft 36. The shape of the side opening 74 is not limited to the illustrated embodiment and may be round, oblong, square, or have another shape. The opening or fenestration 74 illustrated in FIG. 3C has an oblong shape.

In the illustrated embodiment, the opening 74 in the dilator shaft 36 has an oblong shape with its major axis being non-parallel relative to the major axis of the oblong opening 56 in the needle 22. For example the needle opening 56 may extend in a longitudinal direction and the dilator opening 74 may extend in a circumferential direction or vice versa. In other words, the long axis of the dilator opening 74 is disposed generally perpendicular to the long axis of the needle opening 56. As explained in connection with additional embodiments below, these openings 56, 76 can have other shapes, sizes and orientations that preferably obtain a significant degree of overlap to account for manufacturing tolerances and rotational misalignments. For this reason, it is preferred that one of the fenestrations has a greater dimension in at least one direction than the other one of the fenestrations in the same direction. Accordingly, in the illustrated embodiment, the needle fenestration 56 has a longer longitudinal dimension than the longitudinal dimension of the dilator fenestration 74.

The channel formed between the ridges 76 extends in a proximal direction from a point distal to the opening 74. The ridges 76 in the illustrated embodiment are disposed along the dilator shaft 36 and on opposite sides of the dilator shaft 36 so as to balance the dilator shaft 36 within the sheath. In the illustrated embodiment, the ridges 76 form two channels there between. Balancing the dilator within the sheath allows the dilator to apply equal pressure to the inside circumference of the sheath.

The dilator hub 38 may include locking structures at the proximal region 72 and the distal region of the dilator 24. Each locking structure may be a luer type or other type of connection. In the illustrated embodiment, the dilator hub 38 comprises a first luer connection 78, a second luer connection 80, a lip 77, and a base 79. The first luer connection 78 engages to the needle hub 34 on the needle 22 illustrated in FIG. 2E. The second luer connection 80 is disposed distal to the first luer connection 78. In some embodiments, the second luer connection 80 (e.g., a male luer slip connector) can be configured to engage to the sheath hub 42 (e.g., a female luer slip connector) on the sheath 26 illustrated in FIG. 1A. Additionally, the male-female lure slip connectors on these components can be reversed.

FIG. 3D is an enlarged proximal end view of the dilator 24 of FIG. 3A. As shown most clearly in FIG. 3D, the dilator hub 38 comprises an opening 82 that releasably engages the latch element 66 on the needle hub 34 illustrated in FIG. 2E-2F to secure the dilator hub 38 to the needle hub 34 when the needle hub 34 is in the first position 121. Again, the male-female lure slip connectors on the dilator hub and the needle hub 34 can also be reversed in other embodiments.

The color of the dilator 24 may be selected to enhance the contrast between the blood or other fluid and the dilator 24. During blood flash, for example, blood is observed flowing between the dilator 24 and the sheath to confirm proper placement of the needle in a blood vessel. To increase the visibility of the fluid as the fluid flows between the sheath and dilator 24, the sheath is preferably manufactured from a clear or transparent material with the dilator 24 having a color that contrasts with the color of the fluid. For example, the dilator 24 may have a white color to enhance its contrast with red blood. Other colors of dilator 24 could be employed depending on the color of the fluid and the degree of contrast desired. Further, only a portion of the dilator in the region of the blood flash can have the contrasting color with the remainder having a different color. For embodiments that have a channel formed between the needle and dilator 24, the dilator 24 may be manufactured of a clear or transparent material similar to the sheath to allow the physician to observe the blood flash through both the sheath and dilator 24.

FIG. 3E is an enlarged perspective view of another embodiment of a dilator hub 38A. The dilator hub 38A is similar to the dilator hub 38 illustrated in FIG. 3A except that the dilator hub 38A further includes a spin nut or collar 84. The proximal end of the spin nut 84 rotates about an annular groove 73 in the dilator hub 38 (see FIG. 3A). Once disposed within the annular groove 73, the spin nut 84 is inhibited from moving in the distal direction but is free to rotate about the dilator hub 38A. The spin nut 84 can have an interengaging element that locks to a corresponding interengaging element on the sheath 26. In the illustrated embodiment, the spin nut 84 includes an internal thread which engages with an external thread on the sheath hub 42 on the sheath 26 illustrated in FIG. 1A.

The dilator 24 or sheath 26 may separately, or together, form one or more passages to allow air or gas to escape or vent from between the dilator 24 and sheath 26 and/or between the needle and the dilator. The one or more passages may further be sized to inhibit the flow of a liquid, such as blood, while allowing air to pass therethrough. The one or more passages may be in the wall of the sheath 26, the sheath hub, the dilator hub 38, an exposed section of the dilator shaft, and/or formed between adjacent surfaces of the dilator 24 and sheath 26. For example, FIG. 3A shows longitudinally arranged grooves 75 that are formed between adjacent surfaces of the dilator 24 and sheath 26. Such venting passages can also be labyrinth. The adjacent surfaces form a luer slip connection between the sheath 26 and dilator 24.

FIG. 3F is a cross-sectional view taken along lines 3F-3F in FIG. 3A and shows the grooves 75 equally spaced, though not required to be equally spaced, about the circumference of the luer slip surface. The grooves 75 are sized to allow air to escape from between the dilator and the medical article, such as a sheath, when the blood flash occurs. As mentioned above, the one or more passages need not be in the form of a surface groove 75 and instead may be in the form of an opening or passageway.

In the illustrated embodiment, the one or more passages allow air to pass through the luer connection between the sheath and dilator hubs. In the illustrated embodiment, a distal end of the passage 75 is located on the distal side of the luer connection with the proximal end of the passage 75 being located on the proximal side of the luer connection.

The one or more passages may be sized to filter blood or other liquid or may include a filter or other structure that inhibits the passage of a liquid while allowing the passage of air. For example, the sheath itself may include one or more passages in the form of small openings, pores or porous material. Depending on the size of the one or more passages and the expected size of the fluid molecules and formed elements (e.g. red blood cells), the one or more small openings, pores or porous material in the sheath can form a porous vent that allows air to pass yet retain blood.

A method of manufacturing a ridged dilator will now be described. First, an extrusion process is used to create a long tubular body having one or more longitudinal grooves or channels on its outer diameter (OD) or within the substance of the dilator. The long tubular body exceeds the required length of a single dilator and preferably has a length that is many times greater than the length of a single dilator. A manufacturing die is employed in the extrusion process having geometry that reflects the desired geometry for the inside and outside diameters of the dilator and the thickness and circumferential span of the longitudinal grooves or channels or interior channels. In the illustrated embodiment of FIGS. 1-11, the long tubular body includes two longitudinal OD channels on opposite sides of the body to enhance the balance of the dilator within the sheath. However, a single channel can provide a visible indicator for the blood flash. The two channels preferably extend along the length of the extruded tubular body. While the illustrated embodiment includes one or more channel disposed between the dilator and the sheath, one or more channels can in addition or in the alternative be formed between the needle and the dilator, within the dilator, and/or within the sheath. In some embodiments, the dilator 24 thus is made partially or completely from clear, translucent, transparent, or semi-opaque material to visualize the fluid flash within the channel.

With reference back to the illustrated embodiment, the extruded tubular body is cut to the appropriate length for a single dilator. In the preferred method, the two OD grooves extend for the entire length of the cut dilator.

A tipping process is then employed on an end of the cut dilator to reform the tip. An end of the cut dilator is forced into a die/mandrel having geometry that matches the desired geometry of the tip of the finished dilator. The desired geometry is selected depending on, for example, the inside diameter of the sheath. It is desirable for the sheath and dilator to form a close fit or seal near the tip to promote blood flow in the proximal direction up the channel formed between the grooved dilator and sheath. Preferably, the OD of the dilator in the tip region tapers in the distal direction.

When in the die/mandrel, thermal energy is applied to the tip to reform the tip to match the die/mandrel. The thermal energy may be applied by any known technique, including using radiant heating from an infrared or RF heat source. As part of the tipping process, the dilator in the tip region is reformed so that the grooves are essentially removed. With the grooves removed, the dilator is able to form the close fit or seal with the sheath near the tip. The grooves are maintained along the remainder of the dilator on the proximal side of the location where the tip of the sheath 26 sits on the dilator. After removal from the die/mandrel, the tip end of the dilator may be cleaned and cut as necessary to remove any manufacturing remnants.

The one or more fenestrations in the dilator is cut through the dilator near the tip region and in or near the groove. Each fenestration may be cut by any known means, including a drill or laser. Further, the cutting device may be moved with respect to the dilator or vice versa to achieve an oblong or other shape for the fenestration.

The end of the dilator opposite from the tip end can be flared to facilitate over molding the dilator hub onto the dilator.

Figure 4A:
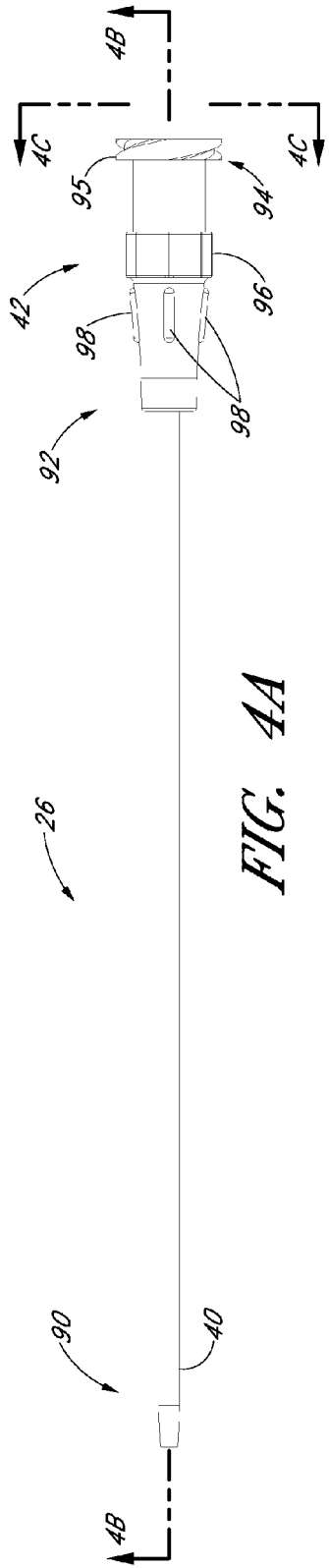
FIG. 4A is a plan view of the sheath from FIG. 1A and shows a sheath hub connected to a proximal end of a sheath.
Figure 4B:
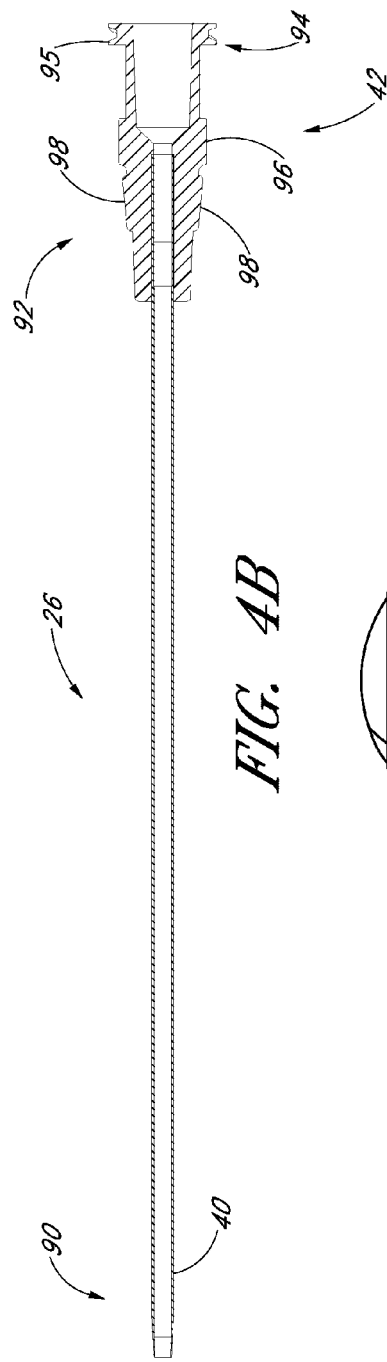
FIG. 4B is a cross-sectional view taken along the lines 4B-4B in FIG. 4A.
Figure 4C:
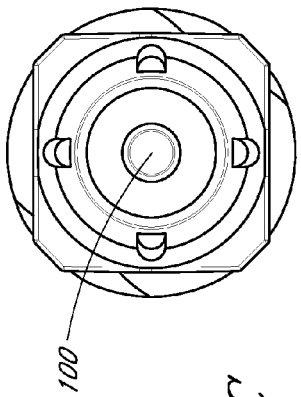
FIG. 4C is an enlarged end view of the sheath from FIG. 4A.
Figure 4D:
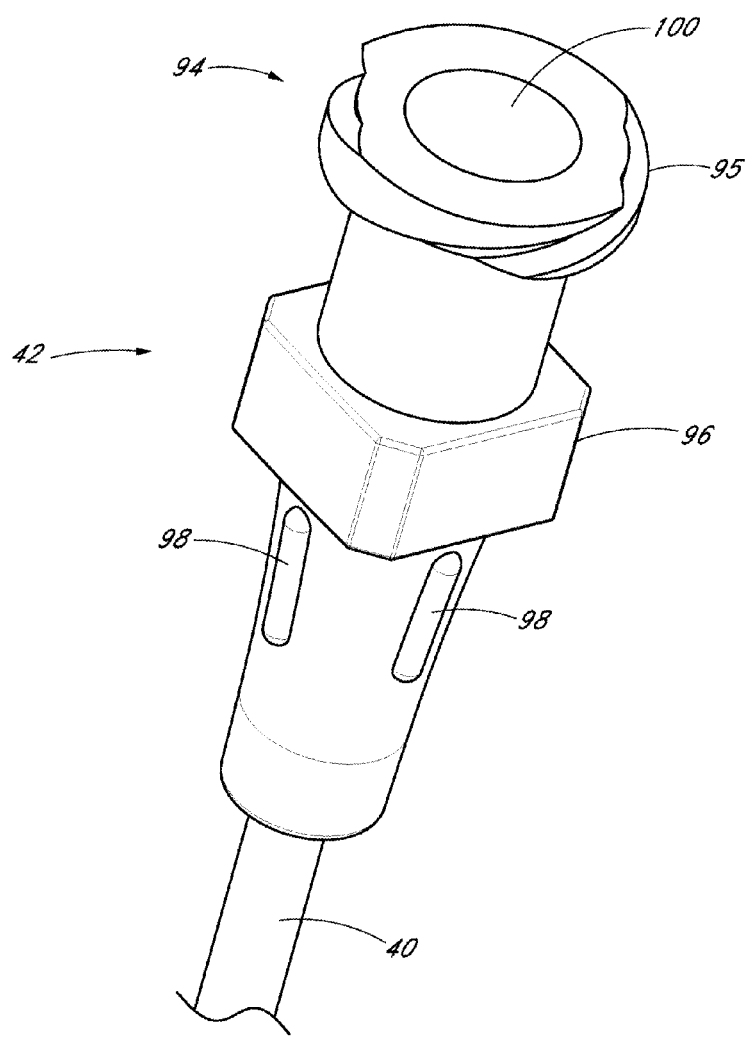
FIG. 4D is an enlarged perspective view of a proximal portion of the sheath from FIG. 4A.

FIG. 4A is a plan view of the sheath 26 of the embodiment depicted in FIG. 1A. FIG. 4B is a cross-sectional view of the sheath 26 of the embodiment depicted in FIG. 4A, taken along line 4B-4B. FIG. 4C is an enlarged proximal end view of the sheath 26 of FIG. 4A. FIG. 4D is an enlarged perspective view of the sheath hub 42 of the sheath 26 of FIG. 4A. As shown in FIGS. 4A-4D, the sheath 26 may comprise a sheath body 40, a sheath hub 42, a distal portion 90, and a proximal region 92. The sheath body 40 may be made partially or completely from clear, translucent, transparent, or semi-opaque material. The sheath body 40 can also include one or more radiopaque markers, such as, for example, barium sulfate stripes. In a preferred embodiment, the sheath includes two such radiopaque stripes disposed on diametrically opposite sides of the body 40.

The sheath body 40 may be a single piece sheath through which a catheter or other medical article (e.g., a guidewire) is inserted into the vessel. In such an embodiment, the sheath body 40 forms a conduit for insertion of the catheter or other medical article (e.g., a guidewire). In addition to providing a conduit, the sheath or a portion of the sheath can form a lumen that is in addition to the lumen(s) of the catheter. For example, an equivalent to a triple lumen catheter can be formed by inserting a dual lumen catheter through the sheath body 40 with the sheath body 40 itself forming a third lumen.

It may be advantageous to remove a portion or the entire sheath body 40 depending on the type of catheter or medical article that is to be inserted into the vessel after employing the access device 20. For example, after the catheter or other medical article is inserted into the vessel, a portion of the sheath body 40 can be separated or peeled-away and removed. A peel-away sheath can include perforations, serrations, skives, or other structures, or include other materials (e.g., PTFE with bismuth) to allow the physician or healthcare provider to remove easily a portion or the entire sheath body 40.

The sheath hub 42 may include a luer slip connection and a lock member 94. The locking member 94 may comprise a locking or attaching structure that mates or engages with a corresponding structure. For example, the lock member 94 can be a luer connection 94 which can be configured to engage with the second luer connection 80 of the dilator hub 38.

The sheath hub 42, as best seen in FIGS. 4C and 4D, preferably is designed so that the locking mechanism or second luer connection 80 of the dilator hub 38 can enter the sheath hub 42 substantially unobstructed. However, in use, once the sheath hub 53 is placed at a desired location over the dilator shaft 36, the physician or healthcare provider can push, pull, or twist the sheath hub 42 and possibly disengage or engage the locking member 94 with a corresponding connector on another medical article. The locking member 94 can be, for example, a luer connection, a protruding bump, dent, etc., that creates a mechanical fit so that the dilator hub 38 and the sheath hub 42 are releasably interlocked. In the illustrated embodiment, the locking member 94 of the sheath hub 42 comprises a luer connection. The sheath hub 42 preferably engages with the corresponding second luer connection 80 on the dilator hub 38. Preferably, the locked position can be disengaged or engaged by pulling, squeezing, pushing or twisting the dilator hub 38 relative to the sheath hub 42.

In some embodiments, the sheath hub 42 can comprise a lip 95. The lip 95 can be threaded to allow the sheath hub 42 to attach to other medical articles with a corresponding locking feature.

The sheath hub 42 preferably comprises one or more surface features to allow the physician or healthcare provider to easily grasp or manipulate the sheath 26 and/or access device 20. In the illustrated embodiment, the sheath hub 42 includes a squared grip 96 and ridges 98.

In additional embodiments, the sheath hub 42 may comprise radially extending wings or handle structures to allow for easy release and removal of the sheath body 40 from other parts of the access device 20. In some applications, the wings are sized to provide the healthcare provider with leverage for breaking apart the sheath hub 42. For example, the sheath hub 42 may comprise a thin membrane connecting the halves of the sheath hub 42. The membrane is sized to keep the halves of the sheath hub 42 together until the healthcare provider decides to remove the sheath hub 42 from the access device. The healthcare provider manipulates the wings to break the membrane and separate the sheath hub 42 into removable halves.

FIG. 5A is a perspective view of the guidewire section 28 of the embodiment depicted in FIG. 1A. FIG. 5B is a plan view of the guidewire section 28 depicted in FIG. 5A, which preferably includes the guidewire hub 46. The guidewire hub 46 can comprise one or more surface features to allow the physician or healthcare provider to easily grasp or manipulate the guidewire hub 46 and/or access device 20. In the illustrated embodiment, the guidewire hub 46 comprises one or more ridges 110. In a pre-loaded state, the outer surface of the guidewire hub 46 engages with a locking mechanism 130 on the track 30 when the guidewire hub 46 is in a third position 125 (example third position 125 illustrated in FIG. 6A).

In some embodiments, the guidewire 44 may form a close fit with the inside diameter of the needle body so as to provide a self-aspirating function when retracted. For example, an outside diameter of the guidewire 44 may be selected to form a close fit with the needle along the length of the guide wire or along only a portion of the guidewire 44.

In some embodiments, the distal end portion of the guidewire can have a reduced diameter in comparison to other sections of the guidewire. The size of such reduced diameter section can be selected to permit fluid to pass to the fenestration 56 in the needle body even when the guidewire has been advanced beyond the distal tip of the needle.

Figure 6A:
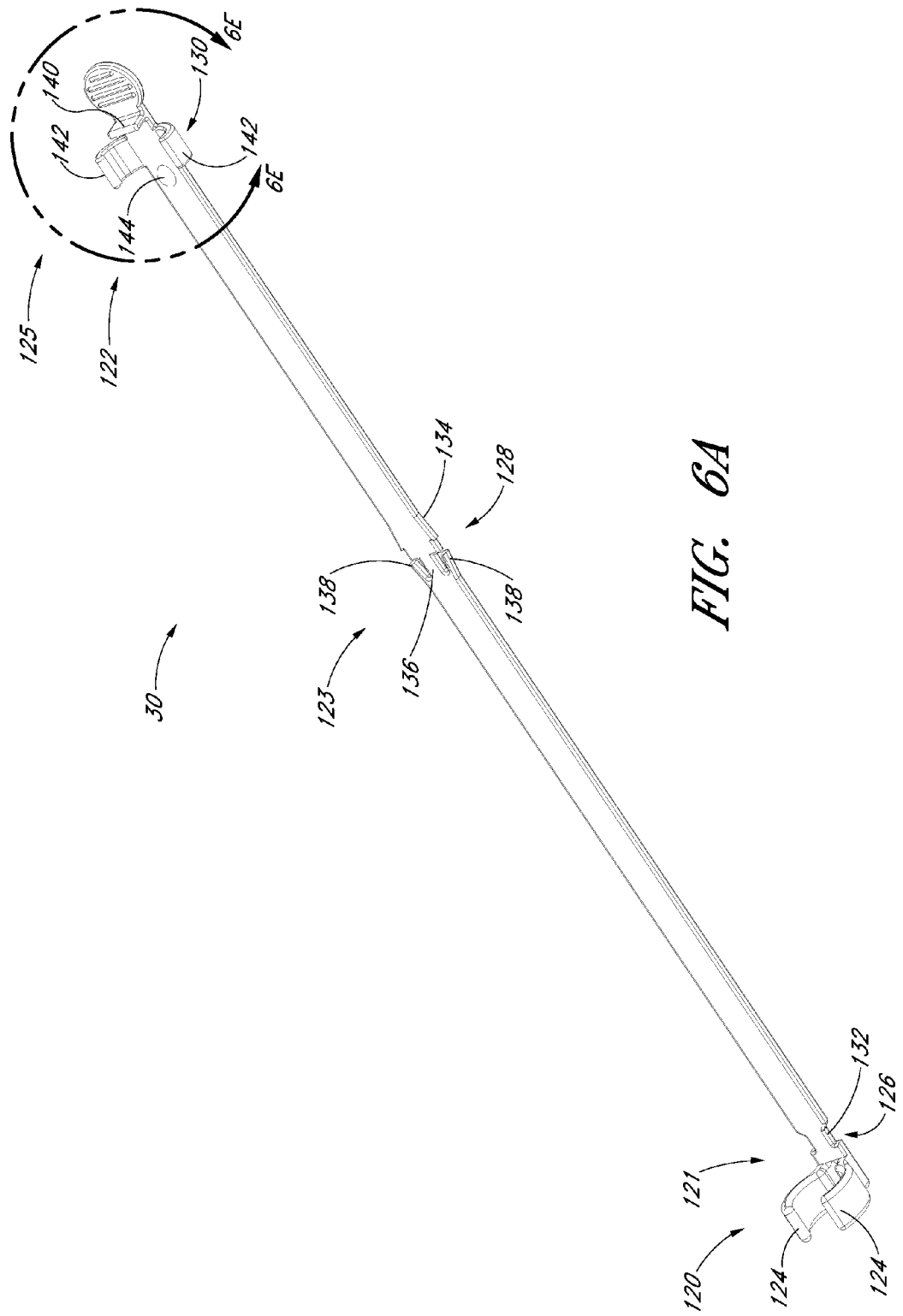
FIG. 6A is a perspective view of a track from FIG. 1A.

FIG. 6A is a perspective view of the track 30 of the embodiment depicted in FIG. 1A. FIG. 6B is a plan view of the track 30 illustrated in FIG. 6A. FIG. 6C is a side view of the track 30 illustrated in FIG. 6A. As shown in FIGS. 6A-6C, the track 30 in the illustrated embodiment comprises a distal portion 120, a proximal portion 122, a distal locking member 124 that connects the track to the dilator hub 38, a locking mechanism 128 that inhibits further proximal and distal movement of the needle hub 34 once the needle hub 34 is slid from the first position 121 to the second position 123 along the track 30, and a locking mechanism 130 that allows the guidewire hub 46 to attach to the track 30 when the guidewire hub is in the pre-loaded state or third position 125. Preferably, the track is made of polycarbonate material; however, as explained below, other materials can be used.

The track 30 may further include a track section 132 of reduced width as shown most clearly in FIGS. 6A and 6B. The reduced width facilitates assembly of the needle hub to the track 30. The illustrated embodiment includes a rib 133 on the distal portion 120 of the track 30. The rib 133 provides additional structural reinforcement between the distal locking member 124 and the remainder of the track 30.

As illustrated in FIG. 1A, the distal locking member 124 connects to the dilator 24 and allows the track 30 to extend proximally from the dilator 24. For example, the locking member 124 can comprise two curved arms 124 that connect to the dilator hub 38 between the dilator hub lip 77 and the dilator hub base 79. The locking member 124 limits movement of the track 30 in a distal or proximal direction relative to the dilator hub 38 but allows the track 30 to rotate freely around the dilator hub 38.

Figure 6E:
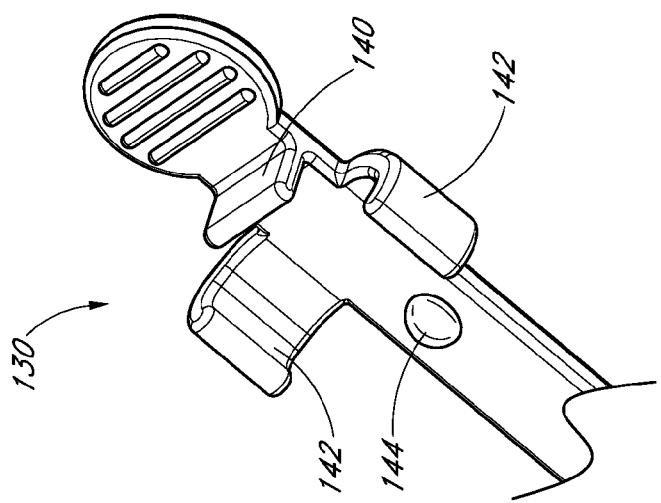
FIG. 6E is an enlarged view of another locking mechanism that locks the guidewire section in a pre-loaded state.
Figure 6D:
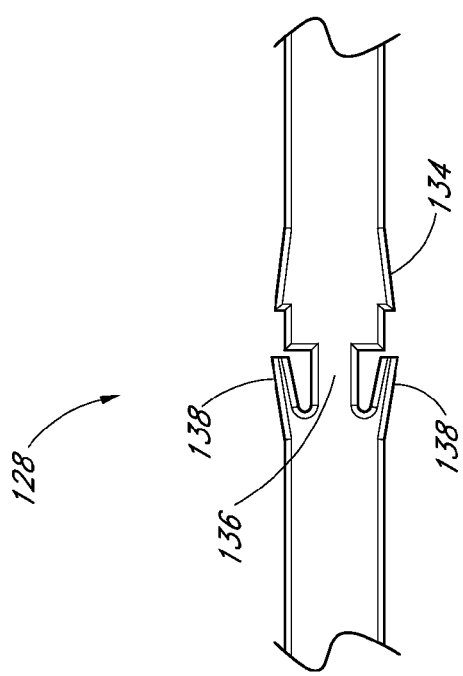
FIG. 6D an enlarged view of the locking mechanism from FIG. 6B.

FIG. 6D is an enlarged view of a portion of the embodiment depicted in FIG. 6B. As shown, the locking mechanism 128 is formed by varying the width of the track in the region of the second position 123. For example, the illustrated embodiment includes a track section 134 of increasing width in the distal direction, a track section 136 of reduced width distal to the track section 134 of increasing width, and two finger elements 138. The two finger elements 138 project from the distal end of the track section 136 toward the proximal end of the track 30 and flare away from the longitudinal axis of the track 30.

FIG. 6E is an enlarged view of a portion of the embodiment depicted in FIG. 6B. The locking mechanism 130 is formed by a clip, clasp or other structure that engages with a portion of the guidewire hub or with a portion of the track 30 when the guidewire hub is in the third position. Some or all of the engagement structure may be part of the track 30, be part of the guidewire hub, or be split between the track 30 and guidewire hub. In the illustrated embodiment, the locking mechanism 130 extends from the track 30 and engages with the guidewire hub. The locking mechanism 130 comprises a rectangular element 140 protruding from the track 30, two track arms 142 projecting from the track 30 distal to the rectangular element 140, and a stop 144 protruding from the track 30 distal to the track arms 142.

In the illustrated embodiment, the locking mechanism between the needle hub and the dilator resides on the proximal side of the dilator hub. In other embodiments, however, the locking mechanism can be disposed at other locations as well. For example, where the locking mechanism includes two pivotal levers which are joined by a locking hinge, the locking mechanism can be disposed radially relative to the needle hub. In such an embodiment, one lever is pivotally coupled to the dilator and the other lever is pivotally coupled to the needle. When the needle hub is moved away from the dilator hub, the levers straighten to a point where the hinge locks. A similar effect can be obtained by a tether limiting proximal movement of the needle hub relative to the dilator beyond a particular point, thereby locking the components together. In a further embodiment, an elongated structure can extend parallel to the needle body from the needle hub within the dilator. Once the needle hub is moved a sufficient distance away from the dilator, additional structure of the locking mechanism (e.g., a detent) engages the elongated structure to inhibit further movement of the needle relative to the dilator. Accordingly, as illustrated by these additional embodiments, the locking mechanism operating between the needle and the dilator can be disposed at a variety of locations relative to the dilator hub.

FIG. 7A is an enlarged plan view of the access device of the embodiment depicted in FIG. 1A pre-loaded with the guidewire. FIG. 7B is a side view of the embodiment depicted in FIG. 7A. FIG. 7C is a cross-sectional view of the embodiment depicted in FIG. 7A along line 7C-7C. FIG. 7D is a proximal end view of the access device 20 of FIG. 7A. In this pre-loaded state, the guidewire hub 46 is locked to the track 30 when the guidewire hub 46 is located in a third position 125. In this position, the guidewire hub 46 can be secured to the track 30 between the rectangular element 140 and the stop 144. For example, the guidewire hub 46 can releasably lock between the rectangular element 140 and the stop 144. In addition, the track arms 142 can further secure the guidewire hub 46 to the track 30. This locking mechanism can arrest unintended rotational and axial movement of the guidewire 44 at least in the distal direction when the guidewire hub 46 is in the third position 125. Of course, the healthcare provider may disengage the guidewire hub 46 from the track 30 to allow distal movement of the guidewire through the access device 20.

In the preloaded-state illustrated in FIGS. 7A-7C, the needle hub 34 is locked to the dilator hub 38 when the needle hub 34 is in the first position 121. Preferably, in the locked position, the openings or fenestrations in the needle and dilator are in register or in alignment with each other. When locked, the needle 22 and the dilator 24 are inhibited from at least unintentional rotational and axial movement relative to each other. By preventing unintentional rotation of the dilator hub with respect to the needle 34, the fenestrations or openings maintain their general alignment.

In the pre-loaded state, the dilator hub 38 is secured to the sheath hub 42. This can inhibit at least unintentional rotational and axial movement between the dilator 24 and the sheath 26. In embodiments where the sheath hub 42 and the dilator 24 have only a luer slip connection, the dilator 24 and sheath hub 42 may rotate relative to each other.

FIG. 8A is a plan view of the embodiment depicted in FIG. 1A that illustrates an operational step of one method of using the access device 20. FIG. 8A depicts the needle body 32 of the access device 20 inserted into a vessel 148, such as a vein. While the described method refers to vascular access, the access device 20 also can be used to access and place a catheter or sheath into other locations within a patient's body (e.g., for draining an abscess) and for other purposes.

FIG. 8B is an enlarged plan view of the portion of the embodiment illustrated in FIG. 8A which is circled by line 8B-8B. FIG. 8C is an enlarged plan view of the portion of the embodiment illustrated in FIG. 8B which is circled by line 8C-8C. FIG. 8D is an enlarged cross-sectional view of the embodiment depicted in FIG. 8C along line 8D-8D.

As noted above, the needle body 32 comprises one or more side openings 56 in its side wall. The dilator shaft 36 comprises one or more side openings 74. The side openings 56, 74 may have the same or different shapes as well as aspect ratios. In the illustrated embodiment, the side opening 56 in the needle body 32 has a different aspect ratio than the side opening 74 in the dilator shaft 36. The side opening 56 in the needle body 32 is elongated in one direction (e.g., substantially parallel to the longitudinal axis of the needle body 32). The side opening 74 in the dilator shaft 36 is elongated in a different direction (e.g., along the circumference of the dilator shaft 36). Having offset elongated openings 56, 74 in the needle body 32 and the dilator shaft 36 increases the likelihood that the openings 56, 74 in the needle body 32 and dilator shaft 36 will be sufficiently aligned so that blood flows through the needle side opening 56 and dilator side opening 74. FIGS. 8A-D illustrate the alignment between only one set of corresponding side openings. Other sets of side openings can also be aligned or be misaligned depending upon the relative orientations of the needle body 32 and the dilator shaft 36.

In the illustrated embodiment, the dilator shaft 36 is coaxially positioned to minimize an annular space 150 between the needle body 32 and the dilator shaft 36. The inner surface 152 of the dilator shaft 36 need not, though it can, lie directly against the outer-surface 154 of the needle body 32. Preferably, in this embodiment, the annular space 150 between the outer-surface 154 of the needle body 32 and the inner surface 152 of the dilator shaft 36 is minimized to inhibit the flow of blood or its constituents (or other bodily fluids) into the annular space 150 between the dilator shaft 36 and needle body 32. Advantageously, this feature minimizes the blood's exposure to multiple external surfaces and reduces the risk of contamination, infection, and clotting.

As illustrated in FIG. 8A, the dilator shaft 36 is coaxially mounted to the needle body 32 such that at least part of one side opening 56 disposed on the needle body 32 is rotationally aligned with at least part of one side opening 74 on the dilator shaft 36. Preferably, the needle body 32 and dilator shaft 36 maintain rotational alignment so that blood flows through the needle side opening 56 and dilator side opening 74.

The sheath body 40, as noted previously, is preferably made partially or completely from clear, semi-opaque, translucent, or transparent material so that when blood flows into the needle body 32, (1) through the needle side opening 56, (2) through the dilator side opening 74, and (3) into a channel 156, the physician or healthcare provider can see the blood. In some modes, the channel 156 is formed between the dilator shaft 36 and the sheath body 40 and defined by one or more ridges 76 on the dilator shaft 36. In some modes, the channel 156 is formed within a wall of the dilator shaft 36 with the dilator shaft 36 preferably comprising a transparent material. Blood will indicate to the physician or healthcare provider that the bevel tip 54 of the needle body 32 has punctured a vessel 148.

In some embodiments, the needle body 32 and dilator shaft 36 may (both) have multiple side openings where some or all of these side openings can be rotationally aligned.

The channel 156 can have an axial length that is almost coextensive with the length of the sheath 26. In other embodiments, the channel 156 can be significantly smaller than the elongated channel 156 just described. For example, but without limitation, the channel 156 can be disposed within a distal, mid and/or proximal portion(s) of the sheath 26. The channel 156 alternatively can have a linear, curved or spiral shape along an axial length of the sheath 26 or can be formed by a plurality of such shapes. The channel 156 may have various thicknesses and span angles. The thickness of the channel 156 can range from almost close to zero to 0.010 inches. Preferably, the channel 156 has a thickness of about 0.0005 to about 0.003 inches. More preferably, the channel 156 can have a thickness of about 0.001 inches to about 0.002 inches. The channel 156 can have a span angle $\Phi$ about the axis of the dilator 24 of about 30 degrees to about 210 degrees or more, but preferably less than 360 degrees. More preferably, the channel 156 can have a span angle $\Phi$ of about 60 to 150. In the illustrated embodiment, the channel 156 spans 120 degrees. The thickness and span angle $\Phi$ can be chosen so as to optimize the capillary action that occurs within the channel 156 as fluid (e.g., whole blood) enters the channel 156 as may further be selected based on the expected pressure in the body cavity and viscosity of the liquid.

Figure 8E:
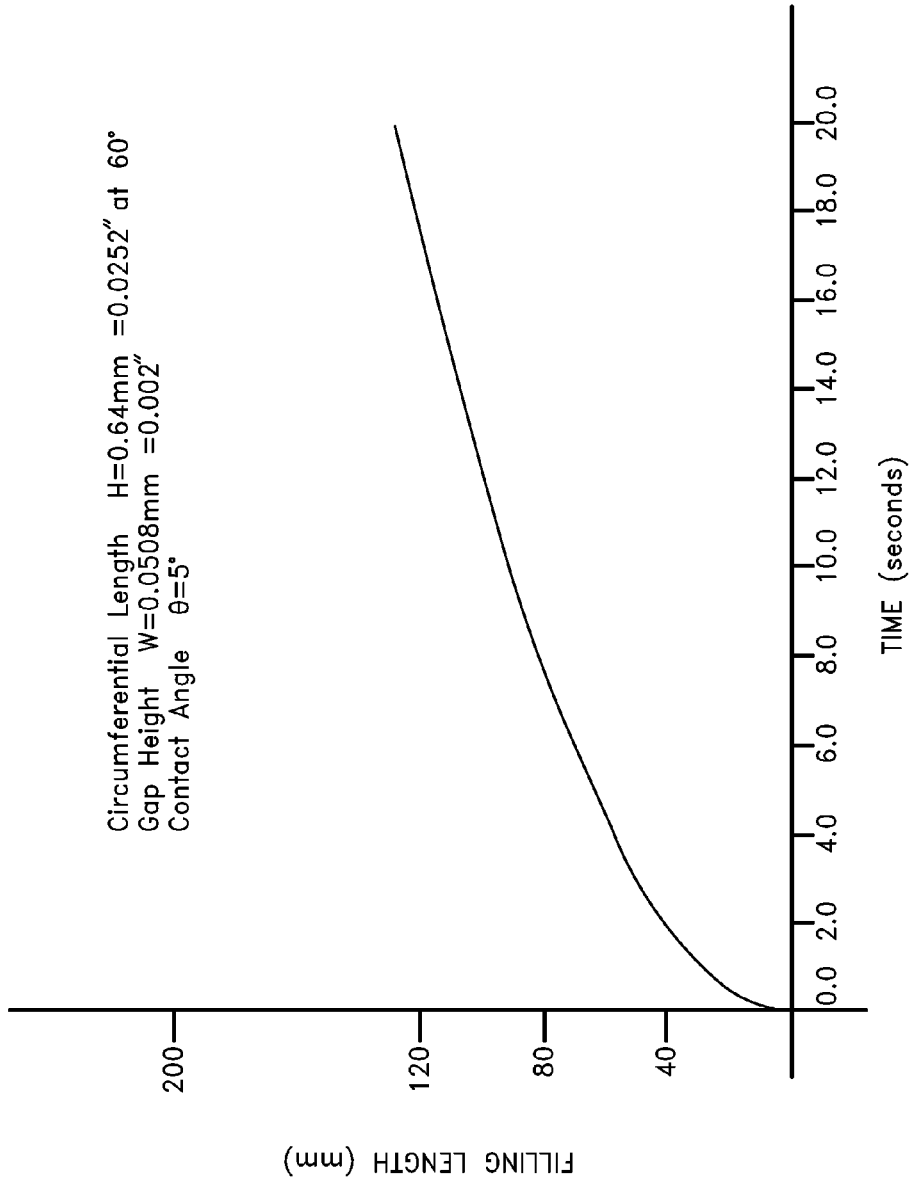
FIG. 8E is a graph showing the rate fluid is drawn up a channel with a gap height width of 0.002 inches.
Figure 8F:
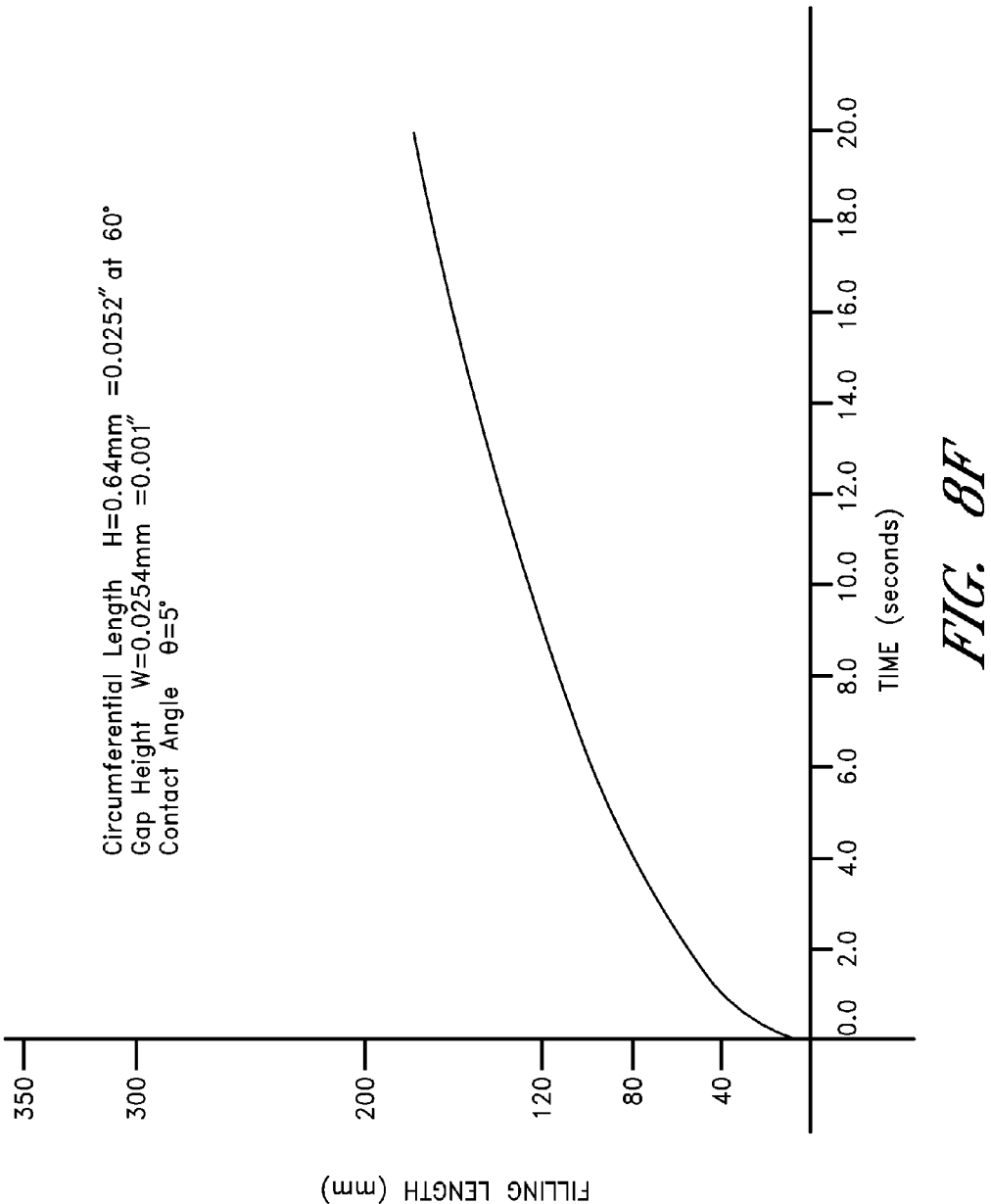
FIG. 8F is a graph showing the rate fluid is drawn up a channel with a gap height width of 0.001 inches.
Figure 8G:
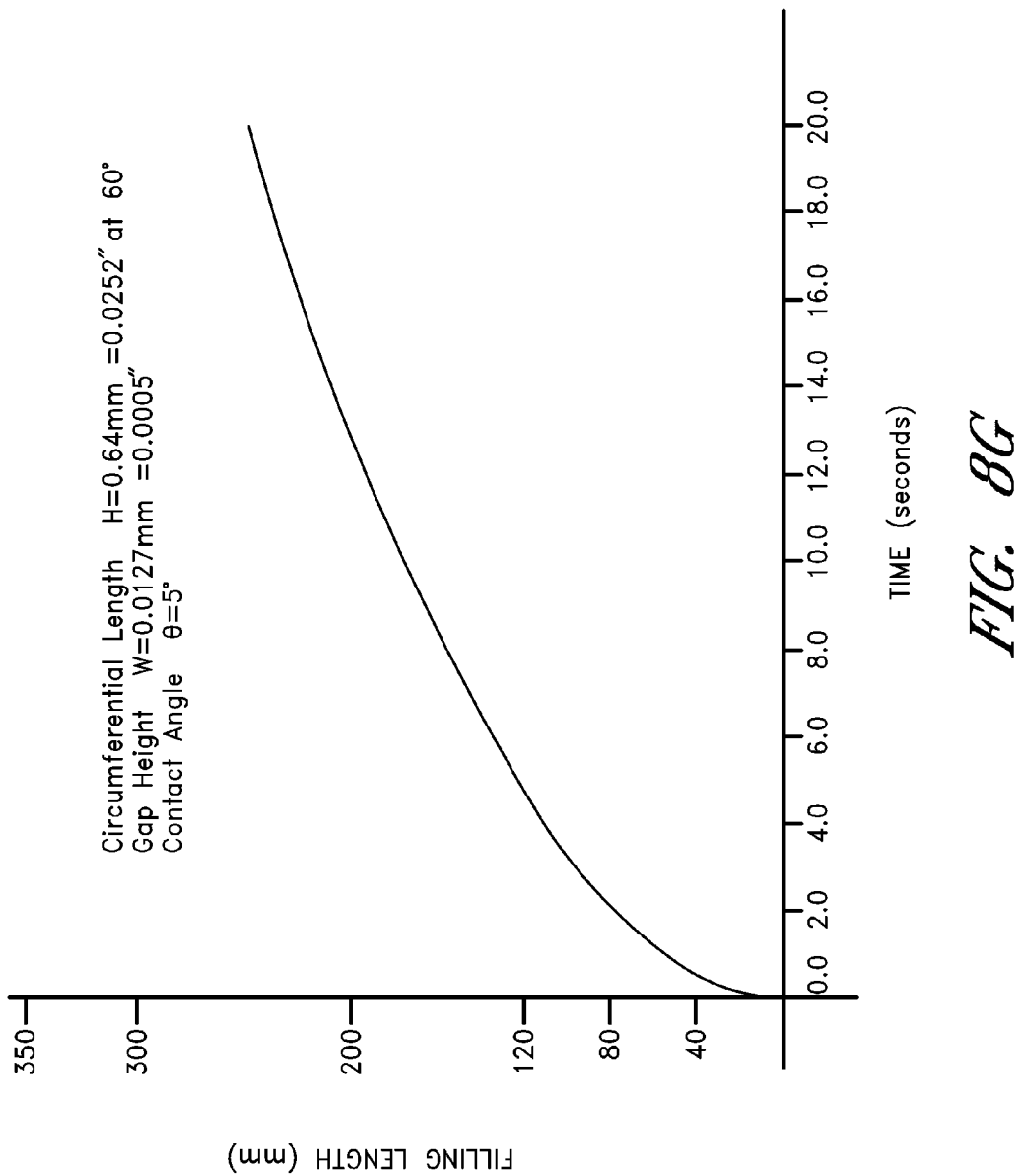
FIG. 8G is a graph showing the rate fluid is drawn up a channel with a gap height width of 0.0005 inches.

FIGS. 8E-8G are graphs of test data illustrating how quickly a fluid is drawn up the surfaces of the channel 156 when the span angle is 120 degrees, the contact angle ($\theta$) is 5 degrees, and the circumferential length (H) is 0.64 mm at 60 degrees. On each graph, the filling length (mm) is plotted on the y-axis, and time (seconds) is plotted on the x-axis. The tests were performed at hydrodynamic pressures similar to pressures experienced in peripheral vessels. FIG. 8E illustrates the rate fluid is drawn up a channel 156 with a gap height width of 0.002 inches, FIG. 8F illustrates the rate fluid is drawn up a channel 156 with a gap height width of 0.001 inches, and FIG. 8G illustrates the rate fluid is drawn up a channel 156 with a gap height width of 0.0005 inches. As shown in FIGS. 8E-G, fluid is drawn up the fastest in a channel with a gap height width of 0.0005 inches, followed by a channel with a gap height width of 0.001 inches, followed by a channel with a gap height width of 0.002 inches.

The shape of the channel 156 described above and the resulting capillary action was optimized for use with whole blood as opposed to other fluids having a different viscosity than whole blood (e.g. leukocytes, pus, urine, plasma). However, the shape of the channel 156 is not limited to the disclosed shape and may be optimized for draining other liquids, such as pus. Further, the shape of the channel 156 described above was optimized for peripherally located vessels where the pressure in the vessel enhances the capillary action and resulting blood flash as well as for vessels located in the regions where the pressure may be low. For example, in the thorax region of the body, the expected pressure in the veins may be lower than in a peripherally located vein when the patient breathes. A different size of the channel for use of the access device 20 in other regions of the body may be employed taking into account the expected pressure within the vessel or body cavity.

Additionally, an outer-surface 160 of the dilator shaft 36 and/or an inner surface 158 of the sheath body 40 can be coated with a substance to promote or enhance the capillary action within the channel 156. For example a hydrophilic substance can be used to coat outer-surface 160 of the dilator shaft 36 and/or the inner surface 158 of the sheath body 40 to enhance capillary action. Similarly, one or both of these components can be made of a hydrophilic material. A hydrophilic substance additionally can be applied to the outer surface of the sheath 26 to act as a lubricant to ease insertion of the sheath 26 into a patient. Other lubricants or lubricous coatings can be used on the exterior of the sheath 26 or at least the outer surface of the sheath can be formed of a lubricous material. Additionally, the sheath 26 can be coated or formed with agents (e.g., heparin), which elute from the sheath, to facilitate the clinical application of the access device 20.

FIG. 8H is a cross sectional view of the embodiment depicted in FIG. 8C along line 8H-8H. In this region of the illustrated access device 20, the sheath body 40 is coaxially positioned to minimize the annular space 157 between the sheath body 40 and the dilator shaft 36 while still allowing relative movement of the sheath body 40 and the dilator shaft 36. The inner surface 158 of the sheath body 40 need not, though it can, lie directly against the outer-surface 160 of the dilator shaft 36. The annular interface 157 between the outer-surface 160 of the dilator shaft 36 and the inner surface 158 of the sheath body 40 may be reduced in this region to inhibit the distal flow of blood or its constituents (or other bodily fluids) from the opening 74 in the dilator shaft 36.

FIG. 8I is an enlarged plan view of the portion of the embodiment illustrated in FIG. 8A which is circled by line 8I-8I. FIG. 8J is a cross-sectional view of the embodiment depicted in FIG. 8I. FIGS. 8I and 8J illustrate the needle hub 34 locked to the dilator hub 38 when the needle hub is in the first position 121. The dilator shaft 36 may be coaxially mounted to the needle body 32 by slipping a hollow section 84 of the dilator shaft 36 over the needle body 32 and releasably securing the dilator hub 38 to the needle hub 34. The proximal end 86 of the dilator hub 38 is configured to mechanically fit and interlock with the needle hub 34.

The dilator shaft 36 may be releasably mounted to the needle body 32 so that the dilator shaft 36 can be mounted and released, or vice versa, from a coaxial position relative to the needle body 32. This locking mechanism can inhibit at least some unintentional rotational and axial movement between the needle 22 and the dilator 24 when the needle hub 34 is in the first position. As shown, the needle hub 34 may have a luer connection 64 that locks to the luer connection 78 of the dilator hub 38. Furthermore, the needle hub 34 may also have latch element 66 that locks to the opening 82 in the dilator hub 38.

In addition, FIGS. 8I and 8J illustrate the dilator hub 38 engaged with the sheath hub 42 when the access device 20 is inserted into a vessel 148. Preferably, the proximal end 86 of the sheath hub 42 is configured to mechanically fit and releasably engaged with the dilator hub 38. As shown, the luer connection 80 in the dilator hub 38 can engage with the lock member 94 of the sheath hub. The resulting friction fit can inhibit at least some unintentional rotational and axial movement between the dilator 24 and the sheath 26 when the access device 20 is inserted into a vessel 148.

Figures 9A, 9B:
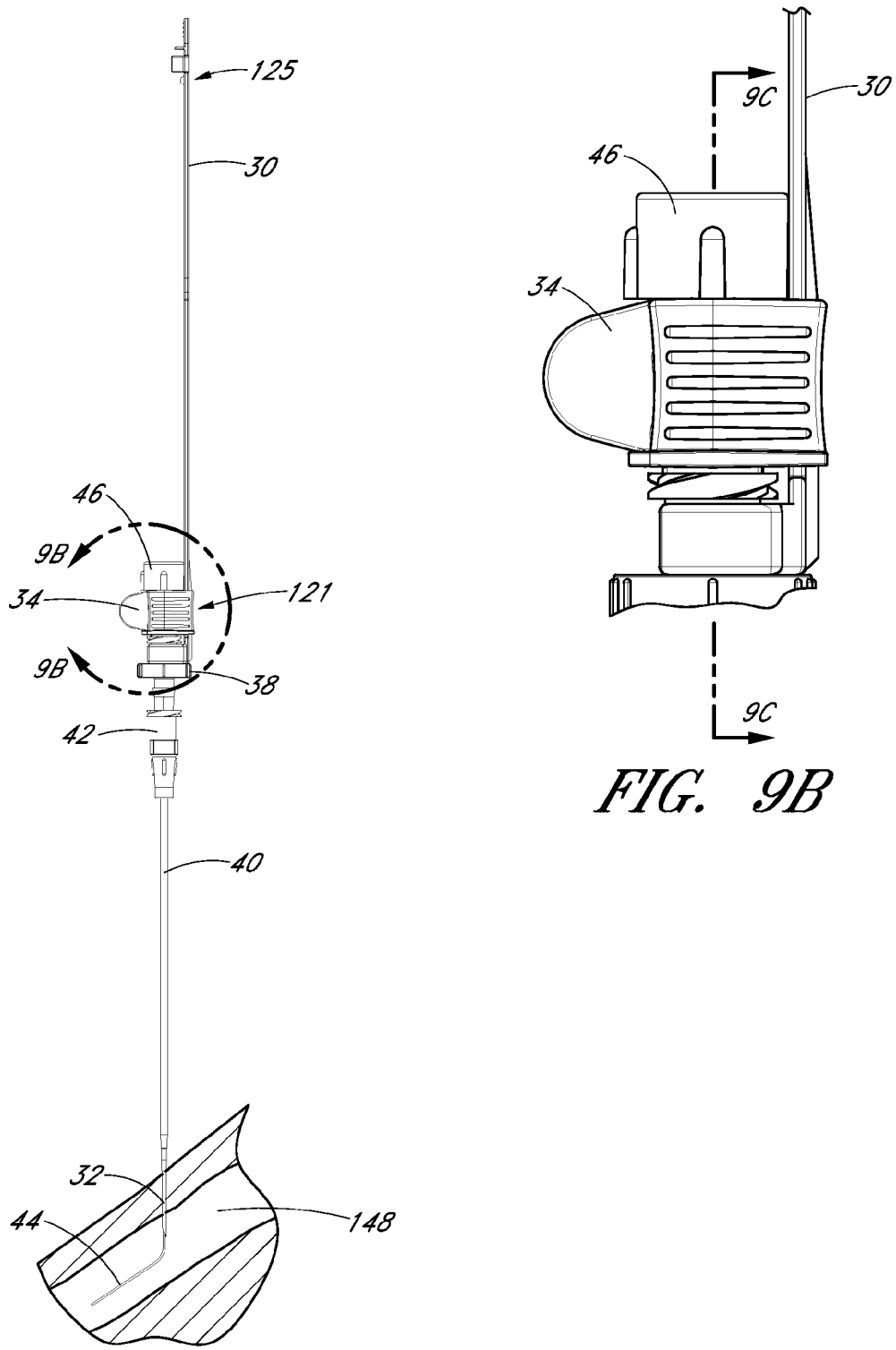
FIG. 9A is a side view of the embodiment depicted in FIG. 1A illustrating the guidewire advanced from the needle tip in a distal direction.
FIG. 9B is an enlarged view of the embodiment depicted in FIG. 9A focusing on the area where the guidewire hub is locked to the needle hub when the needle hub is in the first position.

FIG. 9A is a side view of the embodiment depicted in FIG. 1A that illustrates a further operational step of the access device 20. FIG. 9A depicts the guidewire 44 of the access device 20 advanced in a distal direction into a vessel 148. This can be achieved by advancing guidewire hub 46 from the third position 125 in a distal direction. The guidewire hub 46 is then locked to the needle hub 34 when the needle hub 34 is in the first position 121.

Figure 9C:
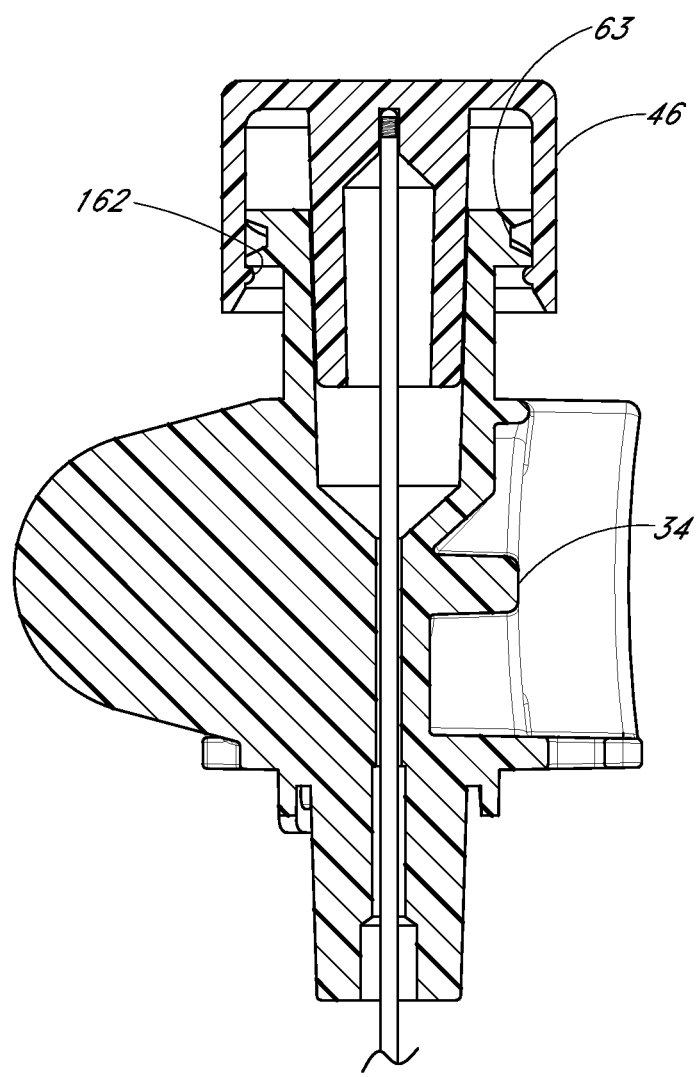
FIG. 9C is a cross-sectional view of the embodiment depicted in FIG. 9B.

FIG. 9B is an enlarged side view of the portion of the embodiment illustrated in FIG. 9A which is circled by line 9B-9B. FIG. 9C is a cross-sectional view of the embodiment depicted in FIG. 9B. FIG. 9C illustrates the locking mechanism between the guidewire hub 46 and the needle hub 34. Preferably, the guidewire hub 46 is configured to mechanically fit and releasably or irreversibly interlock with the needle hub 34. As shown, the guidewire hub 46 includes a nub 162 on the inner surface of the guidewire hub 46. The nub 162 of the guidewire hub can lock onto the needle hub 34 by advancing the guidewire hub 46 in a distal direction until the nub 162 is secured within the threaded groove on the lip of the needle hub 46. In other embodiments, the guidewire hub 46 can lock to the needle hub 34 via corresponding threaded elements.

FIG. 10A is a side view of the embodiment depicted in FIG. 1A that illustrates another operational step of the access device 20. FIG. 10A depicts the dilator shaft 36 and the sheath body 40 advanced in a distal direction into a vessel 148. This can be achieved by releasing the dilator hub 38 from the needle hub 34 and advancing the dilator 24 and sheath 26 in a distal direction relative to the needle hub 34 along the guidewire and needle. FIG. 10A further illustrates the proximal movement of the needle 22 and guidewire section 28 relative to the dilator 24 and the sheath 26. The needle hub 34 will lock to the track 30 when the needle hub 36 reaches the second position 123.

FIG. 10B is an enlarged rear view of the portion of the embodiment illustrated in FIG. 10A which is circled by line 10B-10B. As depicted in FIG. 10B, the needle hub 34 locks onto the track 30 via the locking mechanism 128 in the second position 123. The needle hub tangs 68 slide in a proximal direction over the track fingers 138 and the tangs 68 can lock into place between the track fingers 138 and the track section of increasing width 134. This arrests and, more preferably, substantially irreversibly prevent axial movement of the needle body 32 at least in the distal direction when the needle hub 34 is in the second position 123. In the illustrated embodiment, the locking mechanism 128 irreversibly prevents the needle hub 34 from moving in either the proximal or distal directions once engaged. Furthermore, the distal tip 54 of the needle 22 is drawn into the dilator 24 to sheath the distal tip 54 when the needle hub 34 is in the second position 123. Thus, this locking mechanism 128 inhibits the bevel tip 54 disposed on the distal portion 50 of the needle body 32 from being advanced beyond the distal end of the dilator shaft 36 once the dilator shaft 36 has been advanced over the needle body 32 during use. The dilator shaft 36 thus sheaths the sharp bevel tip 54 of the needle body 32 to inhibit accidental needle sticks from occurring.

FIG. 11A is a side view of the embodiment depicted in FIG. 1A that illustrates the final operational step of the access device 20. FIG. 11A illustrates the removal of the guidewire 44 and the dilator shaft 36 from the vessel leaving the sheath body 40 properly inserted within the vessel 148. FIG. 11B is an enlarged plan view of the portion of the embodiment illustrated in FIG. 11A which is circled by line 11B-11B. As clearly shown in FIG. 11B, the distal end of the dilator shaft 36 and the guidewire 44 extend beyond the sharp bevel tip 54 of the needle body 32 to inhibit accidental needle sticks from occurring.

As noted above, having openings 56, 74 in the needle body 32 and dilator shaft 36 with different aspect ratios will increase the likelihood that the openings 56, 74 in the needle body 32 and dilator shaft 36 will be aligned so that blood flows substantially unobstructed through the needle side opening 56 and dilator side opening 74.

In the following embodiments, structure from one embodiment that is similar to structure from another embodiment share the same root reference number with each embodiment including a unique suffix letter (32, 32A, 32B, etc.). FIG. 12A is a plan view of another embodiment of the openings 56, 74 in the needle body 32 and dilator shaft 36 illustrated in FIGS. 8B and 8C. FIG. 12B is an enlarged cross-sectional view of the embodiment depicted in FIG. 12A along line 12B-12B. FIGS. 12A and 12B depict a needle body 32A with an oblong opening 56A and a dilator shaft 36A with a circular opening 74A. In other embodiments, the needle can have a circular opening and the dilator can have an oblong opening. These embodiments can increase the likelihood that the openings 56A, 74A will be at least substantially aligned so that blood flows through the needle side opening 56A and dilator side opening 74A.

FIG. 13A is a plan view of another embodiment of the openings 56, 74 in the needle body 32 and dilator shaft 36 illustrated in FIGS. 8B and 8C. FIG. 13B is an enlarged cross-sectional view of the embodiment depicted in FIG. 13A along line 13B-13B. FIGS. 13A and 13B depict a needle body 32B with a circular opening 56B and a dilator shaft 36B with a circular opening 74B that is larger than the circular opening 56B in the needle body 32B. In other embodiments, the opening in the dilator can be smaller than the opening in the needle. These embodiments can also increase the likelihood that the openings 56B, 74B will be at least substantially aligned so that blood flows through the needle side opening 56B and dilator side opening 74B.

As noted above, the dilator shaft 36 may have one or more channels 156 formed between ridges 76 to form a conduit or flow path between the sheath body 40 and the dilator shaft 36 to enable the physician or health care provider to view the blood after the bevel tip 54 of the needle body 32 has properly punctured a vessel or the channels may be formed without ridges but by extruding axial indentations of various possible configurations or by forming fully enclosed channels within the dilator shaft or body.

FIG. 14A is a plan view of another embodiment of the ridges 76 depicted in FIG. 8C. FIG. 14B is an enlarged cross-sectional view of another embodiment of the ridges 76 depicted in FIG. 8D. FIGS. 14A and 14B depict two ridges 76C on the inner surface 158C of the sheath body 40C that form at least one channel 156C between the sheath body 40C and the dilator shaft 36C.

FIG. 15A is a plan view of another embodiment of the ridges 76 depicted in FIG. 8C. FIG. 15B is an enlarged cross-sectional view of another embodiment of the ridges 76 depicted in FIG. 8D. FIGS. 15A and 15B depict two ridges 76D on the inner surface 158D of the sheath body 40D and two ridges 76E on the outer surface 160D of the dilator shaft 36D that combine to form a channel 156D between the sheath body 40D and the dilator shaft 36D. For example, if the desired channel thickness is about 0.001 inches, the two ridges 76D on the inner surface 158D of the sheath body 40D can each be about 0.0005 inches thick and the two ridges 76E on the outer surface 160D of the dilator shaft 36D can each be about 0.0005 inches thick.

FIG. 16A is a plan view of another embodiment of the ridges 76 depicted in FIG. 8C. FIG. 16B is an enlarged cross-sectional view of another embodiment of the ridges 76 depicted in FIG. 8D. FIGS. 16A and 16B depict many ridges on the outer surface 160E of the dilator shaft 36E. Between adjacent ridges are splines 76F. The splines 76F form a plurality of channels 156E between the sheath body 40E and the dilator shaft 36E. One or more of the channels 156E can have the same span angle $\Phi$ or different span angles $\Phi$. In the illustrated embodiment the channels 156E have span angles of 120 degrees and 23 degrees. In another embodiment, a single ridge 76 can spiral around the exterior of the dilator along its length.

Figure 17:
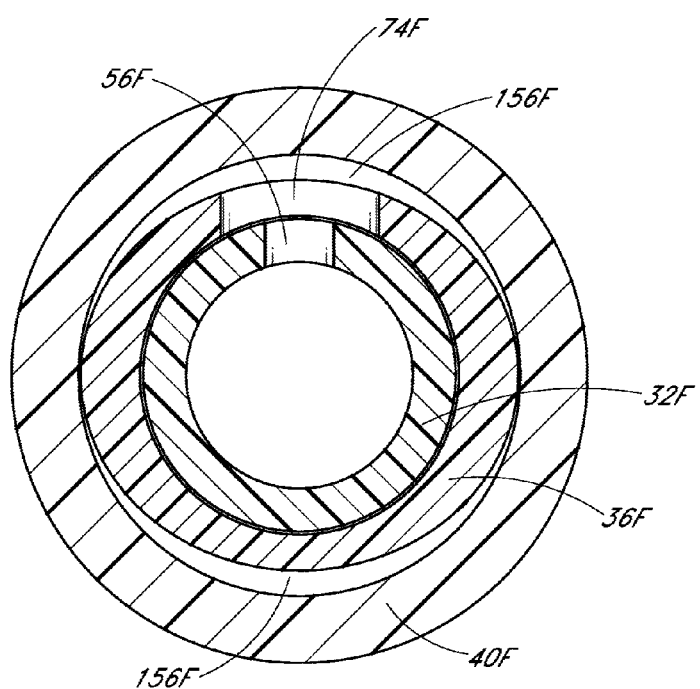
FIG. 17 is an enlarged cross-sectional view through another embodiment of the access device and shows the channel formed between a sheath and a dilator that have dissimilar shapes.

FIG. 17 is an enlarged cross-sectional view through another embodiment of the access device and shows the channel 156F formed between a medical article or sheath body 40F and a dilator shaft 36F that have dissimilar shapes. In the illustrated embodiment, the outer surface of the dilator shaft 36F has an oval shape while the inner surface of the sheath body 40F has a round shape. The oval dilator shaft 36F and the adjacent round sheath body 40F form one or more channels or gaps 156F between the sheath body 40F and the dilator shaft 36F. Of course the shapes of the sheath body 40F and dilator shaft 36F are not limited to round and oval and may include any other combination of dissimilar shapes in adjacent regions of the sheath body 40F and dilator shaft 36F. In some modes, the outer surface of the dilator shaft 36F is oblong and the inner surface of the sheath body or medical article 40F is round. In some modes, the outer surface of the dilator shaft 36F is round and the inner surface of the medical article 40F is square. The gap or channel 156F can follow a longitudinal axis, a spiral path along the longitudinal axis, a linear path along the longitudinal axis or other path along the access device. In some modes, the linear path is parallel to the longitudinal axis. The gap or channel 156F thickness can vary along at least a portion of a length of the gap or channel 156F.

In other embodiments, the channel 156 can be formed by having one complete ridge on the inner surface of the sheath and one complete ridge on the outer surface of the dilator. In other embodiments, the inner surface of the sheath can have two ridges that run 50% of the length of the channel 156 and the outer surface of the dilator can have two ridges that run the remaining 50% of the channel 156.

FIGS. 18 and 19 depict a further embodiment of an access device 20'. As depicted, the guidewire cap 46' and the needle hub 34' can be configured to interengage and/or attach in a preloaded position. The guidewire cap 46' can attach to a side of the needle hub 34' by a variety of means including a screw-thread engagement, a deflecting latch engagement, a wing and slot engagement, a magnetic attachment, or the like. The guidewire 44' can bend to allow this engagement, and further comprise a stiffness chosen to prevent excessive incidental distal movement of the guidewire prior to disengagement, while also minimizing recoil upon disengagement. For example, in some embodiments the stiffness can be chosen to prevent the guidewire from independently flexing completely out of the bore in the needle. As seen in FIGS. 18 and 19, the interlocking or interengaging structure between the guidewire cap 46' and the needle hub 34' is formed in part by an L-shaped arm that extends from the body of the needle hub 34'. The L-shaped arm has a receptacle (e.g., a slot) that receives a portion of the guidewire cap 46' in a snap-fit manner. In other embodiments, the receptacle can receive and retain a portion of the guidewire 44' until the user desires to disengage the cap 46' from the needle hub 34'. In some embodiments, the receptacle can have a serpentine or labyrinth shape to inhibit unintentional disengagement of the guidewire section (e.g., the cap 46' or the guidewire 44') from the needle hub 34'. Further, as depicted the fin 58 has been removed to provide space for the attachment structure. However, in other embodiments they can coexist, such as where the attachment structure is on another side of the needle hub.

Figure 20:
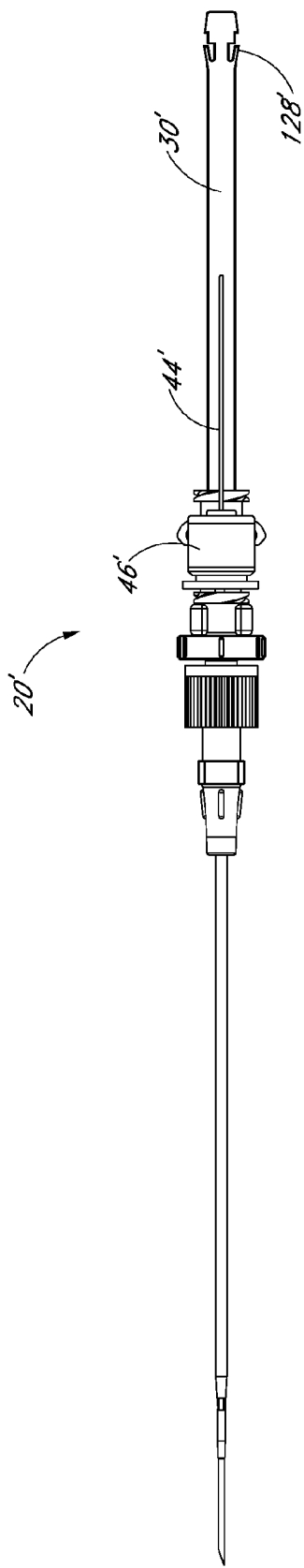
FIG. 20 is a plan view of another embodiment of an access device in an attached position.
Figure 21:
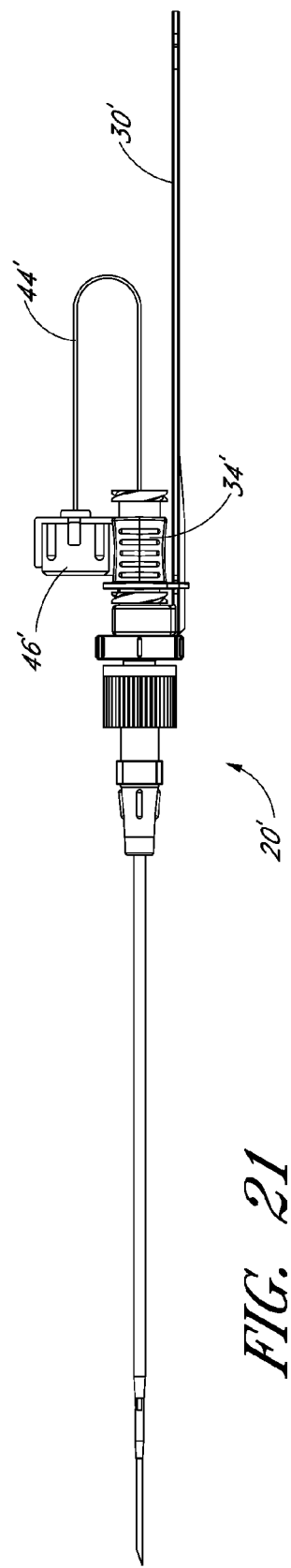
FIG. 21 is a side view of the access device of FIG. 20.

Comparing FIGS. 18 and 19 with FIGS. 20 and 21 indicate two of many possible orientations of the guidewire cap 46' attaching to the needle hub 34'. As depicted, the guidewire cap 46' can engage back to the needle hub 34' (FIGS. 18 and 19) or side to the needle hub (FIGS. 20 and 21). It will be clear from the depicted embodiments that other arrangements are possible. For example, in some embodiments the guidewire cap 46' can attach to the needle body 32, dilator shaft 36, sheath body 40, or any of the hubs. In other embodiments, the guidewire cap 46' can be located somewhere along the length of the guidewire 44, or include a spool for the guidewire.

Further, the track 30', as depicted in FIGS. 18-21 can be substantially shorter than the guidewire. The track need only be long enough to allow sufficient proximal movement of the needle to draw the needle tip into the dilator shaft. As shown, the track 30' only extends to a locking mechanism 128' located at an end of the track. The guidewire, however, can be substantially longer. Consequently, the access device remains easily maneuverable and controllable even with longer needle and guidewire lengths.

The embodiments herein described are comprised of conventional, biocompatible materials. For example, the needle preferably consists of ceramic, a rigid polymer, or a metal such as stainless steel, nitinol, or the like. The other elements can be formed of suitable polymeric materials, such as polycarbonate, nylon, polyethylene, high-density polyethylene, polypropylene, fluoropolymers and copolymers such as perfluoro (ethylene-propylene) copolymer, polyurethane polymers or co-polymers.

As noted above, the present access device can be used to place a catheter at other locations within a patient's body. Thus, for example, but without limitation, the access device can be used as or with a variety of catheters to drain fluids from abscesses, to drain air from a pneumotorax, and to access the peritoneal cavity. In such applications, body fluids flow into the viewing space to indicate when the needle has been properly placed.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. For example, the depicted needle hubs 34, 34' have additional differences aside from interengaging structure and the fine 58, such as the general shape in a side view. However, these shapes are interchangeable between the described embodiments. Thus, it is intended that the scope of the present invention herein disclosed should not be limited by the particular disclosed embodiments described above, but should be determined only by a fair reading of the disclosure and the claims that follow.

What is claimed is:

1. An access device for placing a medical article within a body space, comprising:
    a needle having an elongated needle body with a distal end and a hub, the hub comprising a distal opening from which the needle body extends; and
    a guidewire having first and second ends, the guidewire extending at least partially into the needle hub at the first end and terminating at a cap at the second end,
    wherein the needle hub and the cap have cooperating structure that engage together such that the cap can releasably be attached by the cooperating structure to the needle hub in both of at least two spaced-apart positions.

2. The access device of claim 1, wherein the cap can attach to the needle hub by a screw-thread engagement.

3. The access device of claim 1, wherein the cap can attach to the needle hub by a deflecting latch engagement.

4. The access device of claim 1, wherein the cap can attach to the needle hub by a wing and slot engagement.

5. The access device of claim 1, wherein the hub comprises an L-shaped arm.

6. The access device of claim 5, wherein the L-shaped arm comprises a receptacle.

7. The access device of claim 1, further comprising a track on which the needle hub is mounted.

8. The access device of claim 7, wherein the needle hub can translate across substantially the entire length of the track while mounted.

9. An access device for placing a medical article within a body space, comprising:
    a needle having an elongated needle body with a distal end and a hub, the hub comprising a distal opening from which the needle body extends; and
    a guidewire having first and second ends, the guidewire extending at least partially into the needle hub at the first end and terminating at a cap at the second end,
    wherein the needle hub and the cap have cooperating structure that engage together such that the first end of the guidewire can extend into the needle hub but not through the distal end of the needle while the cap is releasably attached to a side of the needle hub.

10. The access device of claim 9, wherein the cap can attach to the needle hub by a screw-thread engagement.

11. The access device of claim 9, wherein the cap can attach to the needle hub by a deflecting latch engagement.

12. The access device of claim 9, wherein the cap can attach to the needle hub by a wing and slot engagement.

13. The access device of claim 9, wherein the hub comprises an L-shaped arm.

14. The access device of claim 13, wherein the L-shaped arm comprises a receptacle.

15. The access device of claim 9, further comprising a track on which the needle hub is mounted.

16. The access device of claim 15, wherein the needle hub can translate across substantially the entire length of the track while mounted.

17. An access device for placing a medical article within a body space, comprising:
    a needle having an elongated needle body with a distal end and a hub, the hub comprising a distal opening from which the needle body extends; and
    a guidewire having first and second ends, the guidewire extending at least partially into the needle hub at the first end and terminating at a second end,
    wherein the needle hub and the guidewire comprise a means for releasable attachment such that the first end of the guidewire can extend at least partially into an opening in the needle hub and the second end of the guidewire can releasably attach to a side of the needle hub, a portion of the guidewire between the opening of the needle hub and the side of the needle hub being flexed while the first end of the guidewire extends at least partially into an opening in the needle hub and the second end of the guidewire releasably attaches to a side of the needle hub.

18. The access device of claim 17, further comprising a track on which the needle hub is mounted.

19. The access device of claim 18, wherein the needle hub can translate across substantially the entire length of the track while mounted.

* * * * *